(12) United States Patent
Walsh et al.

(10) Patent No.: US 10,911,879 B2
(45) Date of Patent: *Feb. 2, 2021

(54) SPEECH PROCESSOR CASES

(71) Applicant: Advanced Bionics AG, Staefa (CH)

(72) Inventors: Thomas Patrick Walsh, Valencia, CA (US); Carla Mann Woods, Beverly Hills, CA (US); Richard C. Ross, Westlake Village, CA (US); Rankiri Tissa Karunasiri, Valencia, CA (US); Anthony K. Arnold, Valencia, CA (US); Lakshmi Narayan Mishra, Carlsbad, CA (US)

(73) Assignee: Advanced Bionics AG, Staefa (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/371,009

(22) Filed: Mar. 31, 2019

(65) Prior Publication Data

US 2019/0230456 A1 Jul. 25, 2019

Related U.S. Application Data

(60) Continuation of application No. 15/379,398, filed on Dec. 14, 2016, now Pat. No. 10,291,993, which is a division of application No. 14/886,068, filed on Oct. 18, 2015, now Pat. No. 9,554,221, which is a continuation of application No. 14/185,726, filed on Feb. 20, 2014, now Pat. No. 9,179,229, which is a division of application No. 13/275,592, filed on Oct. 18, 2011, now Pat. No. 8,660,658, which is a continuation-in-part of application No. 12/607,427, filed on Oct. 28, 2009, now Pat. No. 8,155,748, which is a division of application No. 11/121,700, filed on May 4, 2005, now Pat. No. 7,630,772, said application No. 13/275,592 is a continuation-in-part of application No. 11/121,756, filed on May 4, 2005, now Pat. No. 8,068,914.

(60) Provisional application No. 60/568,450, filed on May 5, 2004.

(51) Int. Cl.
*A61N 1/36* (2006.01)
*H04R 25/00* (2006.01)
*H04R 25/02* (2006.01)

(52) U.S. Cl.
CPC ......... *H04R 25/65* (2013.01); *A61N 1/36038* (2017.08); *H04R 25/02* (2013.01); *H04R 25/556* (2013.01); *H04R 25/602* (2013.01); *H04R 25/604* (2013.01); *H04R 2225/021* (2013.01); *H04R 2225/31* (2013.01); *H04R 2225/61* (2013.01); *H04R 2460/17* (2013.01)

(58) Field of Classification Search
CPC ............................ H04R 25/65; A61N 1/36038
USPC .......................................................... 607/57
See application file for complete search history.

(56) References Cited

U.S. PATENT DOCUMENTS

| | | |
|---|---|---|
| 1,422,877 A | 7/1922 | Maxfield |
| 3,906,170 A | 9/1975 | Guice |
| 4,248,237 A | 2/1981 | Kenny |

(Continued)

FOREIGN PATENT DOCUMENTS

| | | |
|---|---|---|
| EP | 1271898 A1 | 1/2003 |
| EP | 1271898 B1 | 4/2006 |

(Continued)

*Primary Examiner* — Nadia A Mahmood
(74) *Attorney, Agent, or Firm* — Henricks Slavin LLP

(57) ABSTRACT

Apparatus and methods for converting one type of speech processor unit into another type of speech processor unit.

22 Claims, 24 Drawing Sheets

(56) References Cited

U.S. PATENT DOCUMENTS

| | | |
|---|---|---|
| 4,347,956 A | 9/1982 | Berger |
| 4,419,995 A | 12/1983 | Hochmair et al. |
| 4,456,797 A | 6/1984 | Olsen |
| D278,761 S | 5/1985 | Fuller |
| 4,532,930 A | 8/1985 | Crosby et al. |
| 4,545,381 A | 10/1985 | Bournay |
| 4,562,590 A | 12/1985 | DeLage |
| 4,584,718 A | 4/1986 | Fuller |
| 4,682,363 A | 7/1987 | Goldfarb et al. |
| 4,683,587 A | 7/1987 | Silverman |
| 4,727,599 A | 2/1988 | Rappaport et al. |
| 4,819,647 A | 4/1989 | Byers et al. |
| 5,249,234 A | 9/1993 | Butler |
| 5,294,988 A | 3/1994 | Wakabayashi et al. |
| 5,386,084 A | 1/1995 | Risko |
| 5,603,726 A | 2/1997 | Schulman et al. |
| 5,637,417 A | 6/1997 | Engmark et al. |
| 5,706,940 A | 1/1998 | Amarello |
| 5,824,022 A | 10/1998 | Zilberman et al. |
| 5,896,453 A | 4/1999 | Speaks |
| 5,948,006 A | 9/1999 | Mann |
| 6,067,474 A | 5/2000 | Schulman et al. |
| 6,092,707 A | 7/2000 | Bowes |
| 6,236,969 B1 | 5/2001 | Ruppert |
| 6,272,382 B1 | 8/2001 | Faltys et al. |
| 6,308,101 B1 | 10/2001 | Faltys et al. |
| 6,317,313 B1 | 11/2001 | Mosgrove et al. |
| 6,390,971 B1 | 5/2002 | Adams et al. |
| 6,396,769 B1 | 5/2002 | Polany |
| 6,456,487 B1 | 9/2002 | Hetterick |
| 6,614,722 B2 | 9/2003 | Polany et al. |
| 6,697,674 B2 | 2/2004 | Leysieffer |
| 6,748,093 B2 | 6/2004 | Topholm |
| 6,748,094 B1 | 6/2004 | Tzviskos et al. |
| 6,761,266 B2 | 7/2004 | Popish |
| 6,775,389 B2 | 8/2004 | Harrison et al. |
| 6,778,858 B1 | 8/2004 | Peeters |
| 6,785,566 B1 | 8/2004 | Irizarry |
| 6,810,289 B1 | 10/2004 | Shaquer |
| 6,922,591 B2 | 7/2005 | Single |
| 6,954,405 B2 | 10/2005 | Polany et al. |
| 7,003,128 B2 | 2/2006 | Boonen |
| 7,058,452 B2 | 6/2006 | Dahlberg |
| 7,069,063 B2 | 6/2006 | Halkosaari et al. |
| D528,213 S | 9/2006 | Darley et al. |
| 7,113,611 B2 | 9/2006 | Leedom et al. |
| 7,123,733 B1 | 10/2006 | Borowsky et al. |
| 7,142,926 B2 | 11/2006 | Crawford |
| 7,158,376 B2 | 1/2007 | Richardson et al. |
| 7,167,572 B1 | 1/2007 | Harrison et al. |
| 7,171,014 B2 | 1/2007 | Morales et al. |
| 7,174,214 B2 | 2/2007 | Seligman |
| 7,230,823 B2 | 6/2007 | Richardson et al. |
| 7,263,032 B2 | 8/2007 | Polany et al. |
| 7,312,984 B2 | 12/2007 | Richardson et al. |
| 7,400,917 B2 | 7/2008 | Wood et al. |
| 7,535,799 B2 | 5/2009 | Polany et al. |
| 7,630,772 B1 | 12/2009 | Walsh et al. |
| 7,660,633 B2 | 2/2010 | Darley et al. |
| 7,729,774 B1 | 6/2010 | Lynch et al. |
| 8,068,914 B1 | 11/2011 | Walsh et al. |
| 8,155,748 B1 | 4/2012 | Walsh et al. |
| 8,352,037 B2 | 1/2013 | Darley et al. |
| 8,364,275 B2 | 1/2013 | Darley et al. |
| 8,660,568 B2 | 2/2014 | Walsh et al. |
| 9,179,229 B2 | 11/2015 | Walsh et al. |
| 9,554,221 B2 | 1/2017 | Walsh et al. |
| 9,906,881 B2 | 2/2018 | Darley et al. |
| 10,291,993 B2 | 5/2019 | Walsh et al. |
| 2002/0193136 A1 | 12/2002 | Halkosaari et al. |
| 2003/0031336 A1 | 2/2003 | Harrison et al. |
| 2003/0036782 A1 | 2/2003 | Hartley |
| 2004/0073275 A1 | 4/2004 | Maltan et al. |
| 2004/0196996 A1 | 10/2004 | Feitel |
| 2005/0181745 A1 | 8/2005 | Wood et al. |
| 2007/0106344 A1 | 5/2007 | Darley et al. |
| 2007/0270180 A1 | 11/2007 | Takagi |
| 2008/0298627 A1 | 12/2008 | Bonebright et al. |
| 2009/0017884 A1 | 1/2009 | Rotschild |
| 2010/0137941 A1 | 6/2010 | Darley et al. |
| 2010/0137942 A1 | 6/2010 | Darley et al. |
| 2012/0041517 A1 | 2/2012 | Walsh et al. |
| 2012/0189148 A1 | 7/2012 | Bewley et al. |
| 2018/0146311 A1 | 5/2018 | Darley et al. |
| 2018/0160244 A1 | 6/2018 | Darley et al. |

FOREIGN PATENT DOCUMENTS

| | | |
|---|---|---|
| WO | WO 2001087014 A2 | 11/2001 |
| WO | WO 2003076012 A1 | 9/2003 |
| WO | WO 2005007049 A1 | 1/2005 |
| WO | WO 2006071210 A1 | 7/2006 |
| WO | WO 2007102158 A2 | 9/2007 |
| WO | WO 2008150642 A1 | 12/2008 |
| WO | WO 2012098443 A2 | 7/2012 |

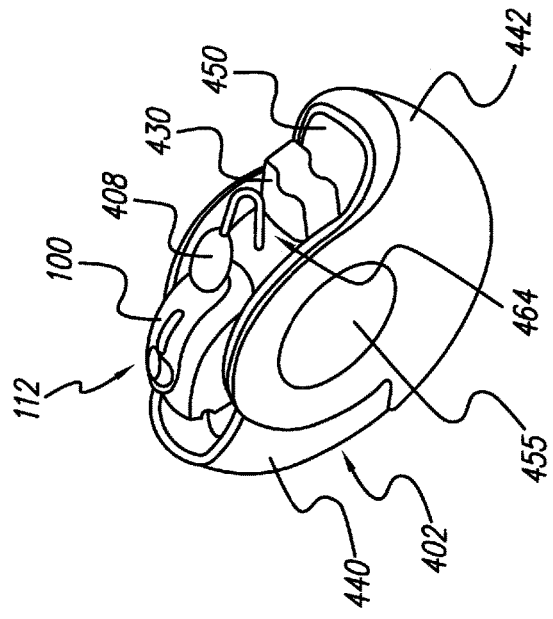
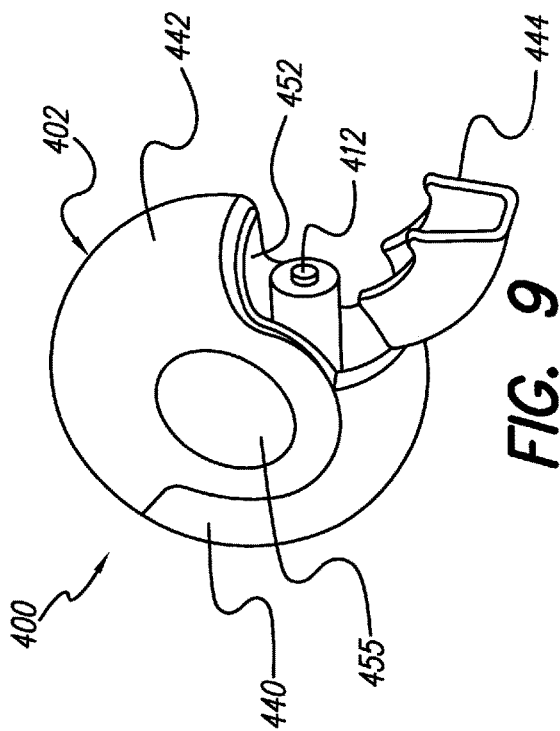
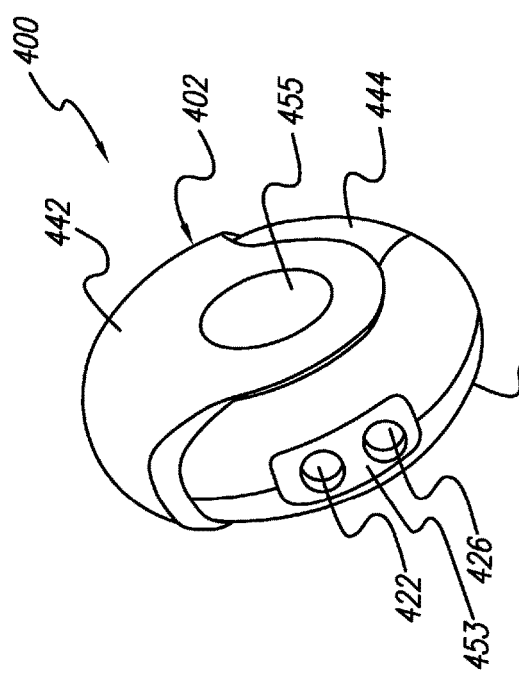
FIG. 7
FIG. 8
FIG. 9

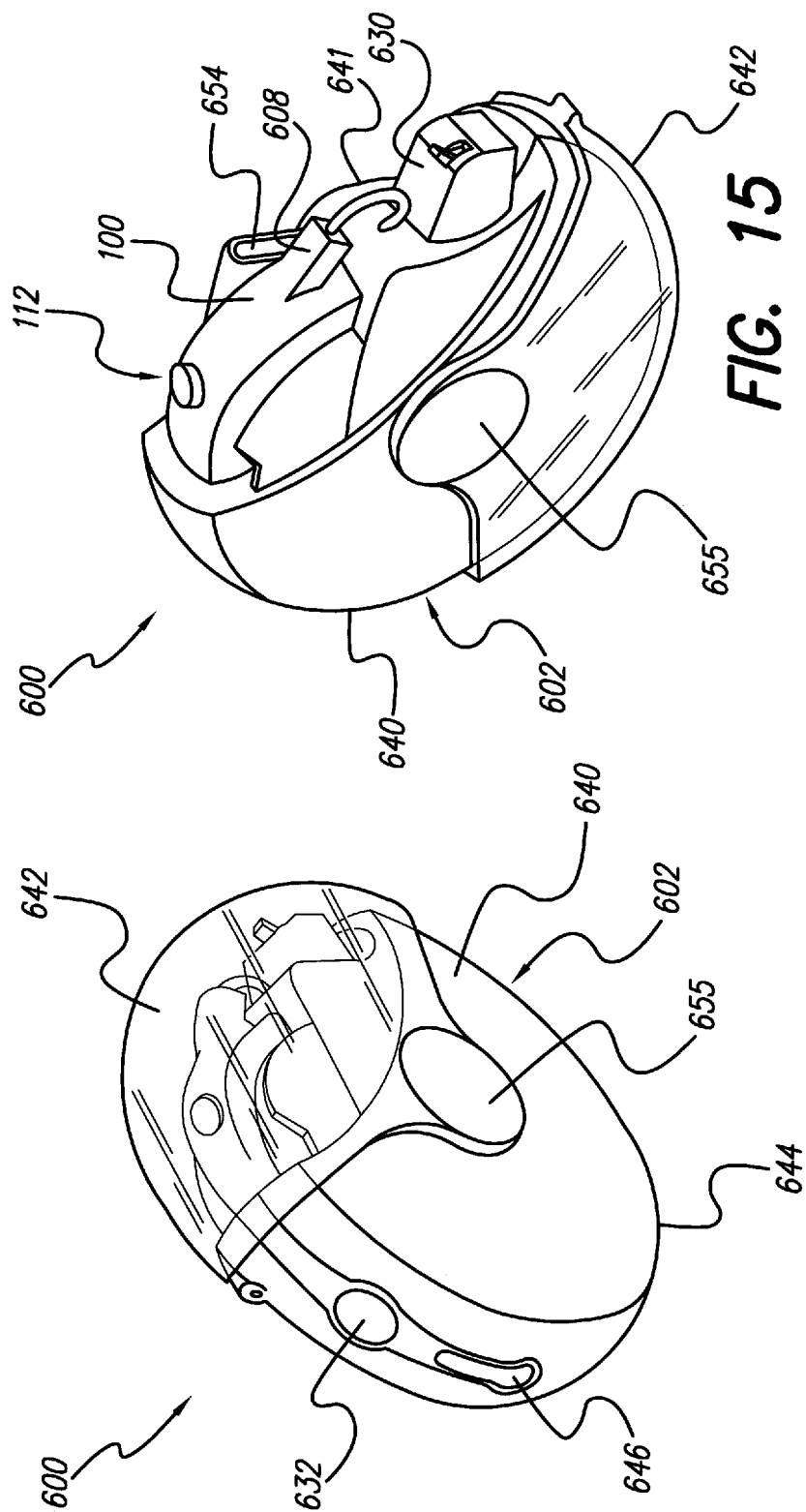

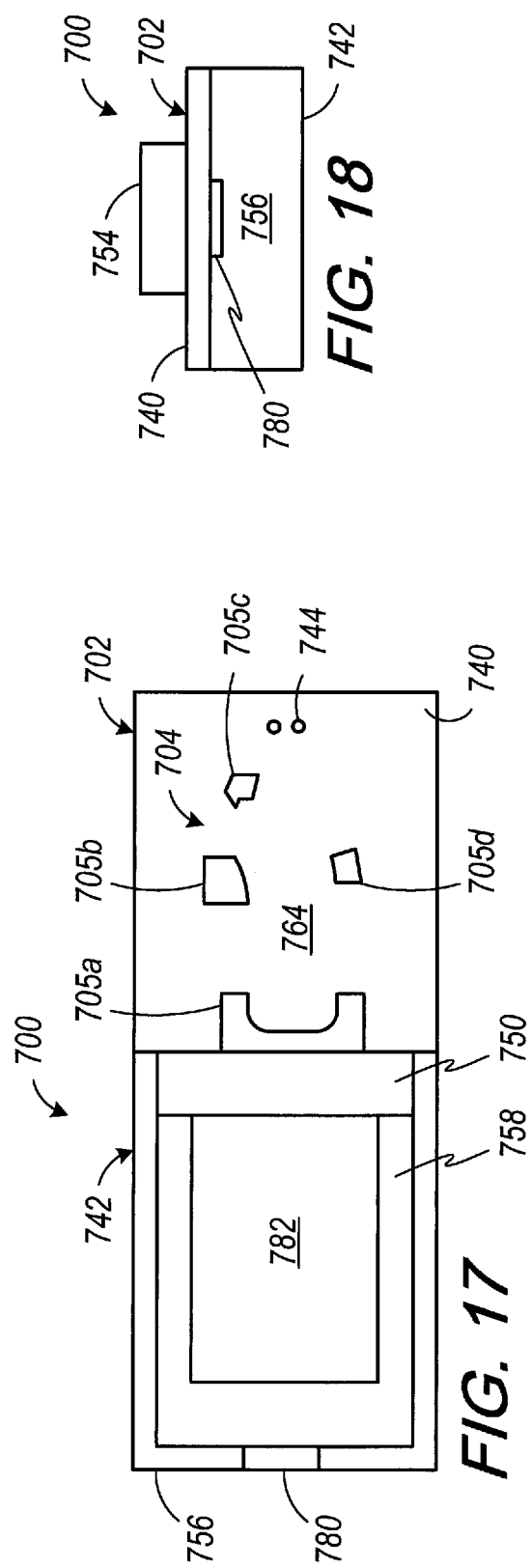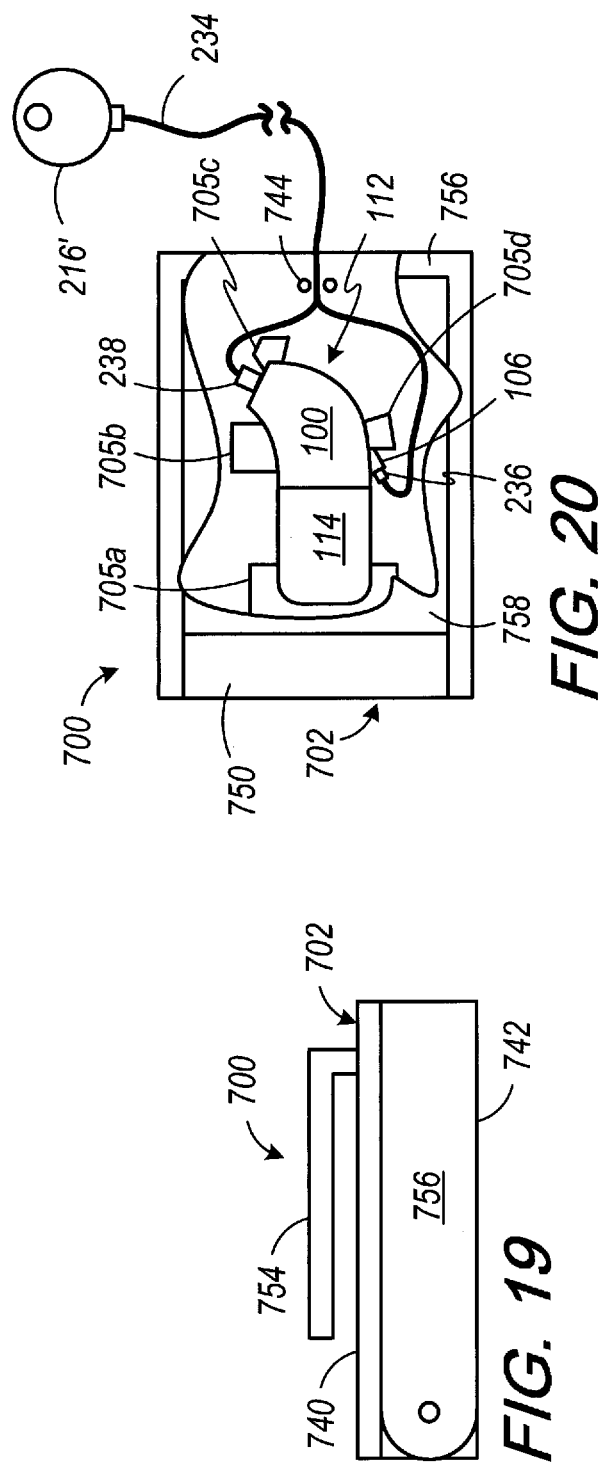

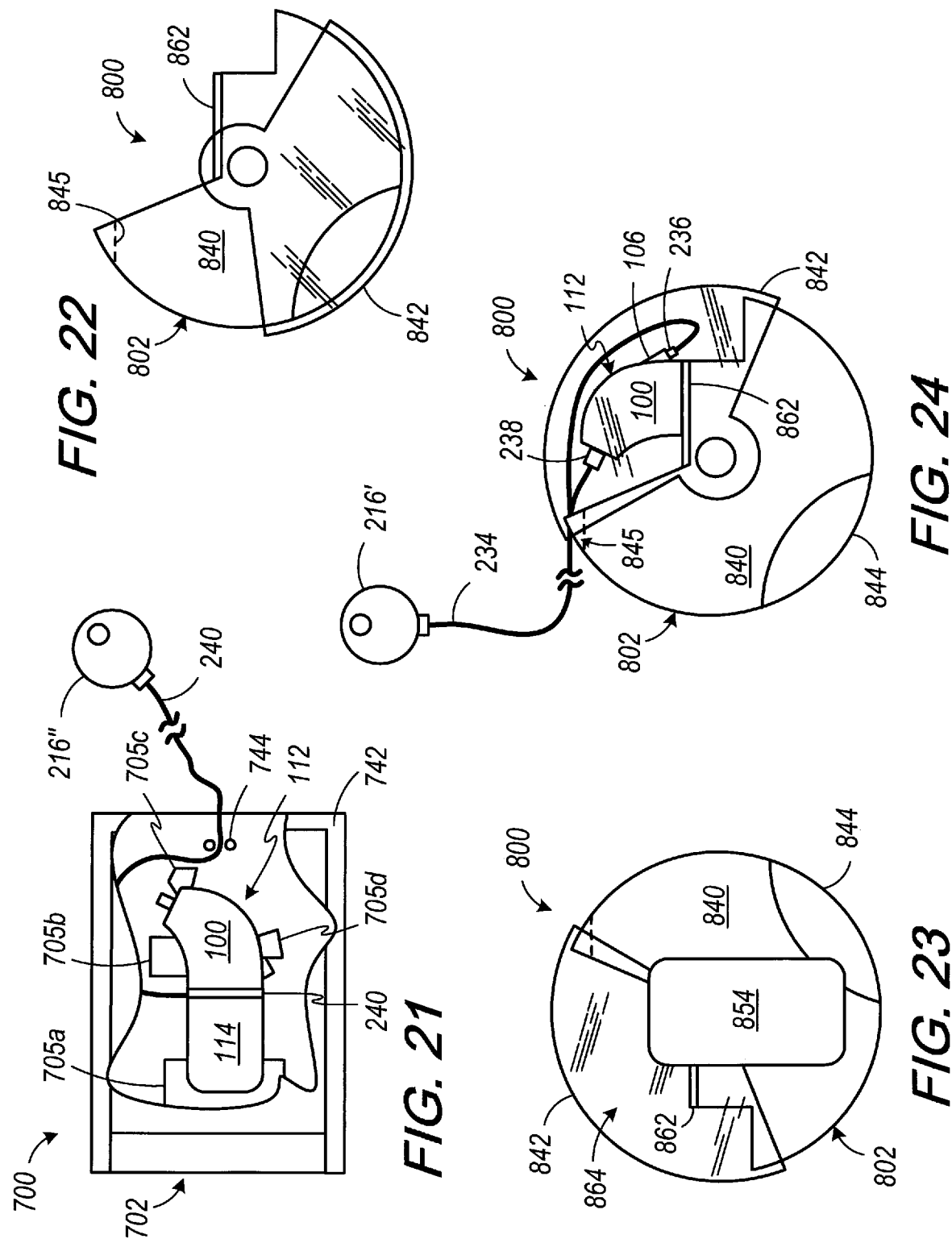

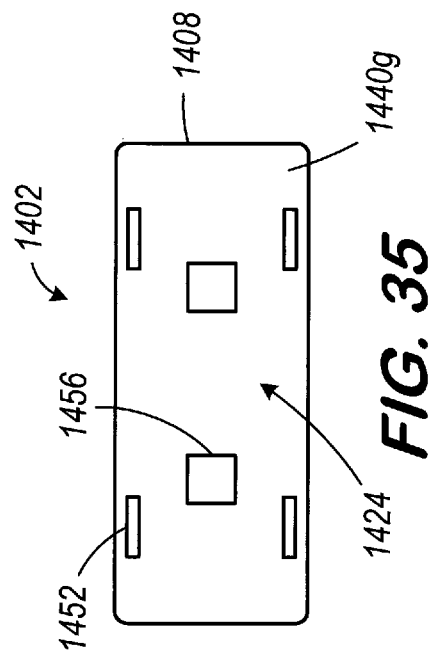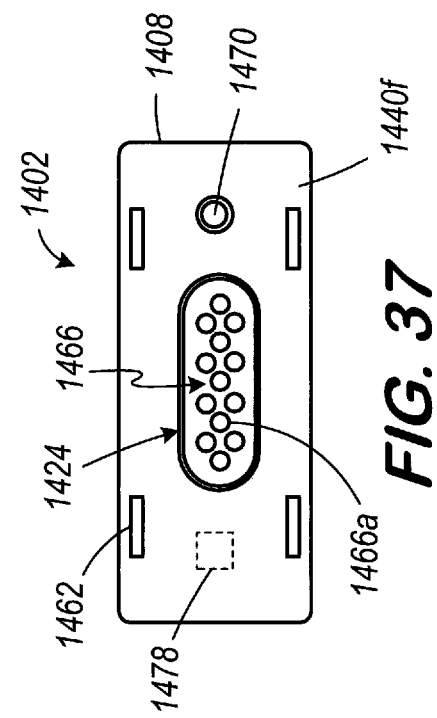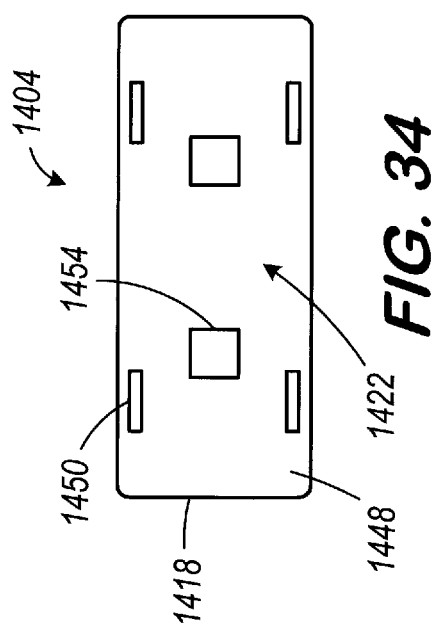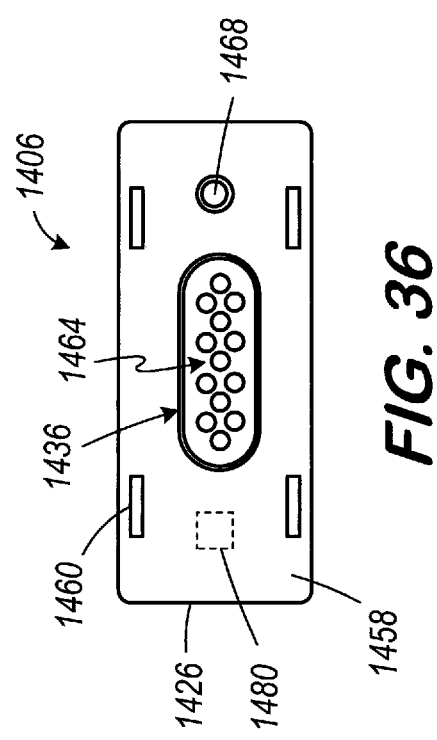

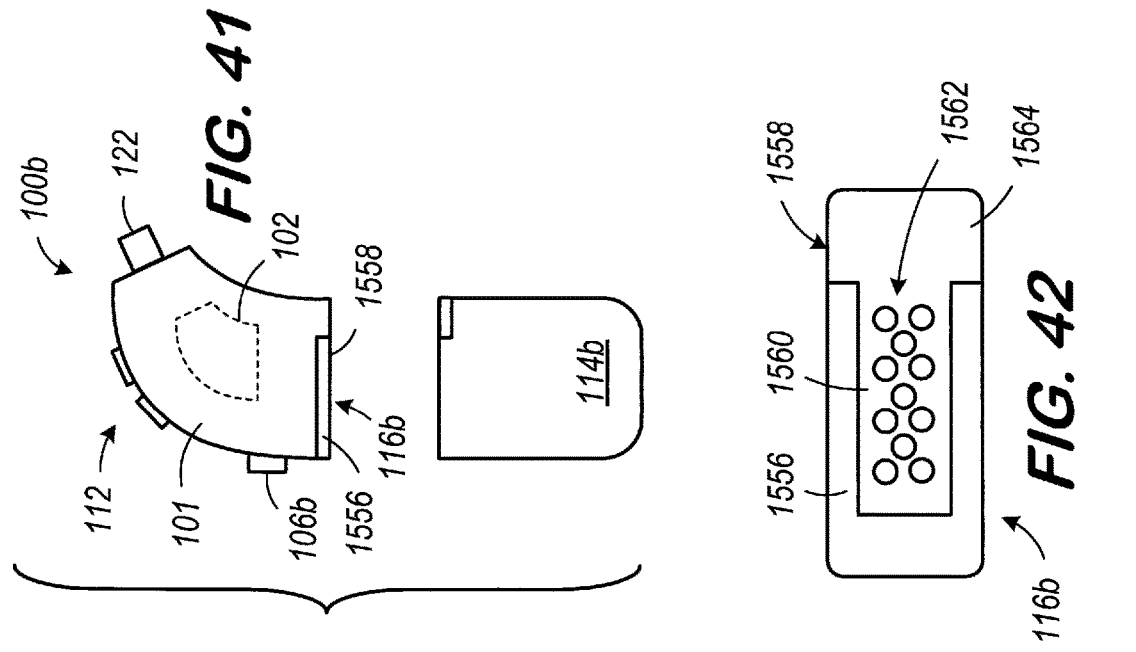
FIG. 41
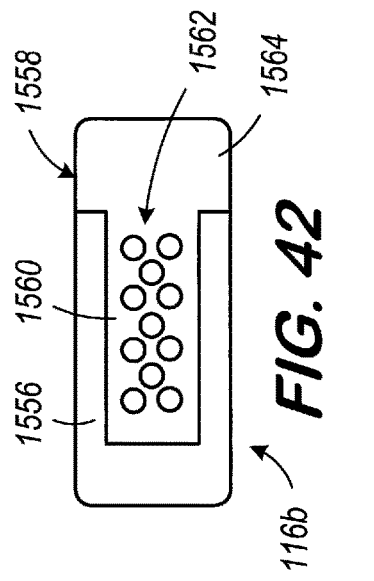
FIG. 42
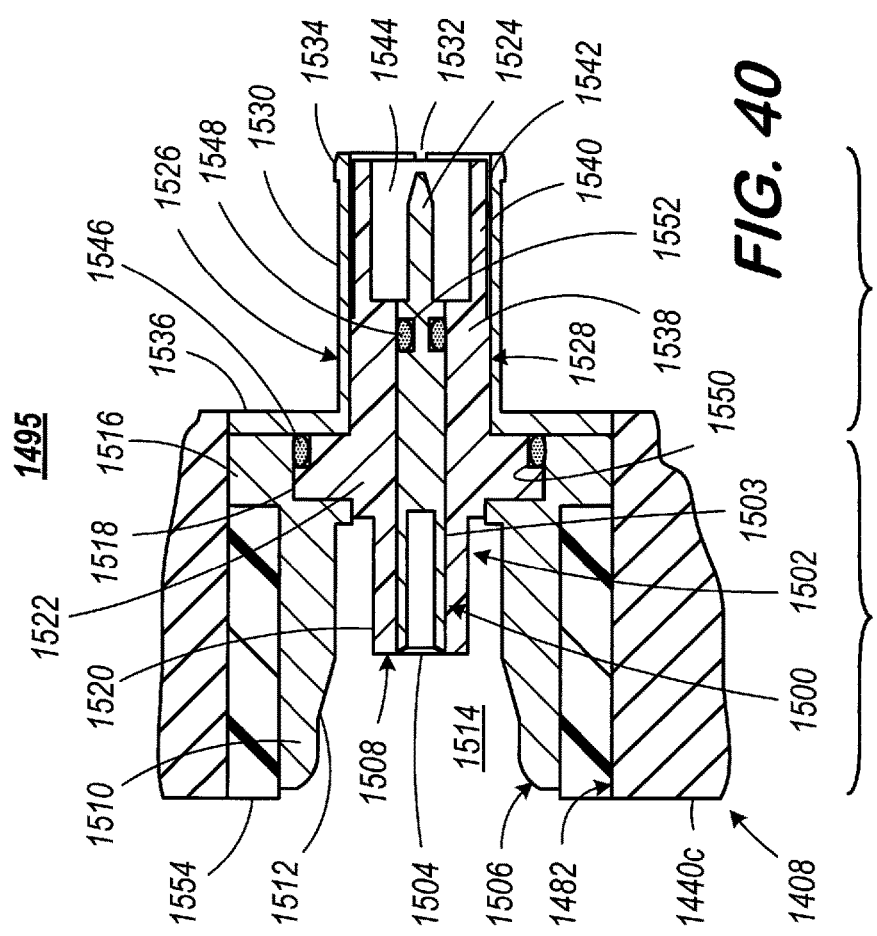
FIG. 40
FIG. 43

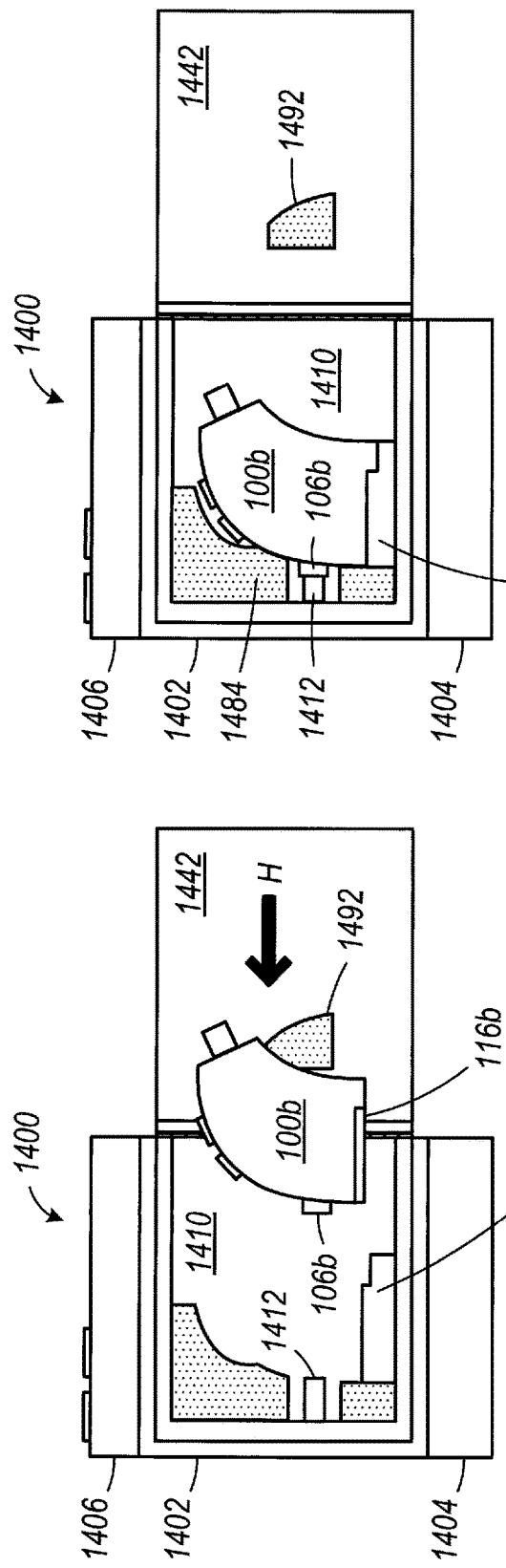
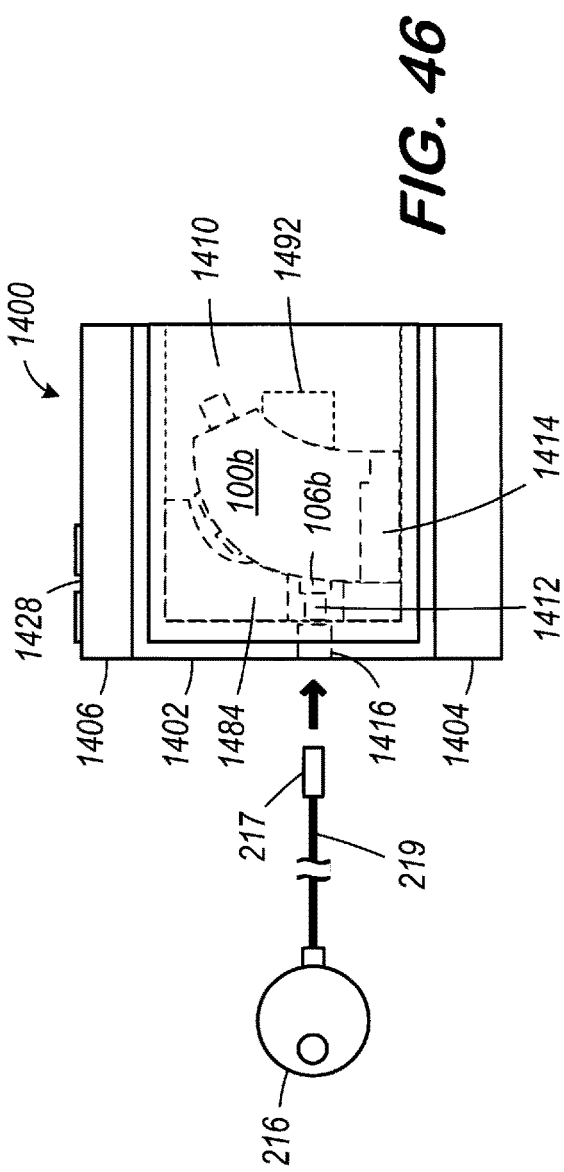

SPEECH PROCESSOR CASES

CROSS-REFERENCE TO RELATED APPLICATIONS

This application is a continuation of U.S. application Ser. No. 15/379,398, filed Dec. 14, 2016, now U.S. Pat. No. 10,291,993, which is a divisional of U.S. application Ser. No. 14/886,068, filed Oct. 18, 2015, now U.S. Pat. No. 9,554,221, which is a continuation of U.S. application Ser. No. 14/185,726, filed Feb. 20, 2014, now U.S. Pat. No. 9,179,229, which is a divisional of U.S. application Ser. No. 13/275,592, filed Oct. 18, 2011, now U.S. Pat. No. 8,660,658, which is a continuation-in-part of U.S. application Ser. No. 12/607,427, filed Oct. 28, 2009, now U.S. Pat. No. 8,155,748, which is a divisional of U.S. application Ser. No. 11/121,700, filed May 4, 2005, now U.S. Pat. No. 7,630,772, which claims the benefit of U.S. Provisional Patent App. Ser. No. 60/568,450, filed May 5, 2004.

U.S. application Ser. No. 13/275,592, filed Oct. 18, 2011, now U.S. Pat. No. 8,660,658, is also a continuation-in-part of U.S. application Ser. No. 11/121,756, filed May 4, 2005, now U.S. Pat. No. 8,068,914, which claims the benefit of U.S. Provisional Patent App. Ser. No. 60/568,450, filed May 5, 2004.

Each application listed above is incorporated herein by reference in its entirety.

BACKGROUND

1. Field

The present inventions relate generally to speech processors (also commonly referred to as "sound processors") such as, for example, the speech processors in implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a speech processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Speech Processor With Remote Control" and incorporated herein by reference in its entirety.

As alluded to above, ICS systems typically include an implantable device, a speech processor unit, a microphone that is in communication with the speech processor unit, and a headpiece that is in communication with both the speech processor unit and the implantable device. In one type of ICS system, the speech processor unit is worn behind the ear and, accordingly, this type of speech processor unit is often referred to as a behind-the-ear speech processor unit (or "BTE unit"). The BTE unit is typically secured to the user with a removable ear hook and, in many cases, a microphone is carried by the ear hook. An on-board microphone is also carried by the BTE unit itself. Another type of speech processor unit is the body worn speech processor unit (or "body worn unit"). The body worn unit, which is larger and heavier than a BTE unit, is typically worn on the user's belt or carried in the user's pocket. The body worn unit will typically have a larger battery and a larger control interface with greater functionality than that found on a BTE unit. Microphones used in combination with body worn units are often incorporated into the headpiece.

The present inventors have determined that conventional ICS systems are susceptible to improvement. For example, body worn units are preferable to BTE units in the case of infants and toddlers. BTE units tend to be too big for infants, and toddlers tend to remove and/or damage BTE units. Body worn units, on the other hand, can be attached to a harness that positions the speech processor unit on the infant or toddler's back, where it is difficult for the infant or toddler to reach. A BTE unit may, however, be more suitable once the child reaches an age (e.g. 5 years) at which he or she is less likely to damage the speech processor unit. Parents must then purchase a second speech processor unit, which is quite expensive. Even in those instances where insurance coverage or government subsidy (collectively "insurance") provides for two speech processor units, and the parents elect to receive a BTE unit in addition to the body worn unit, the body worn unit may be of limited utility once the child is old enough to switch to a BTE unit. Moreover, if the BTE unit is lost or damaged, the child will be forced to switch back to a body worn unit because there is no spare BTE unit.

The present inventors have also determined that adults face similar obstacles with respect to BTE units and body worn units. For example, many adults prefer the smaller BTE units for most everyday activities, but prefer body worn units for sports and other activities for which an ear hook mounted BTE unit is simply unsuitable. Here too, the user is faced with a choice—elect to obtain a BTE unit or a body worn unit through insurance and, if possible, purchase the other type of speech processor unit. Moreover, even in those instances where insurance provides for two speech processor units, the user will not have a spare BTE unit if he or she elects to obtain one of each. Users are also forced to carry both speech processor units with them if they intend to switch from the BTE unit to the body worn unit and back without returning home.

SUMMARY

A speech processor case in accordance with a present invention includes a housing with a speech processor storage area, a first housing headpiece connector configured to be connected to the speech processor unit headpiece connector, and a second housing headpiece connector operably connected to the first housing headpiece connector and configured to be connected to a headpiece.

A speech processor case in accordance with one embodiment of a present invention includes a housing with a speech processor storage area and a housing power connector associated with the speech processor storage area and configured to be connected to the speech processor unit power connector.

A method in accordance with one implementation of a present invention includes the steps of positioning a behind-the-ear speech processor unit in a speech processor case, including at least one of a headpiece connector and a power connector, and connecting the behind-the-ear speech processor unit to the at least one of a headpiece connector and a power connector.

A method in accordance with one implementation of a present invention includes the steps of docking a behind-the-ear speech processor unit within a speech processor case and operably connecting the behind-the-ear speech processor unit to a cochlear implant by way of the speech processor case.

A case in accordance with one embodiment of a present invention includes a housing with a behind-the-ear sound unit storage area configured to receive behind-the-ear sound unit and means for mounting the behind-the-ear sound unit within the storage area.

A case in accordance with one embodiment of a present invention includes a case main portion including a housing with an interior speech processor storage area configured to enclose a speech processor unit, an internal housing headpiece connector configured to be connected to a speech processor unit headpiece port, and an external housing headpiece connector operably connected to the internal housing headpiece connector, configured to be connected to the headpiece cable connector.

A case in accordance with one embodiment of a present invention includes a case main portion including a housing with an interior speech processor storage area configured to enclose the speech processor unit, a power supply, an internal power connector operably connected to the power supply.

A system in accordance with one embodiment of a present invention includes a BTE unit and a BTE storage case. The BTE storage case may include a housing, a BTE storage area within the BTE storage case, a case power supply, an external control panel and means for electrically connecting the power supply and the external control panel to the BTE unit.

Such cases and methods are advantageous for a variety of reasons. For example, the cases and methods allow the users of BTE units to enjoy the benefits of body worn units as well as a BTE unit without the expense associated with obtaining two speech processor units. More specifically, the present cases and methods allow a BTE unit to be converted into a body worn unit by simply placing the BTE unit into the case. While the BTE unit is safely stored within the case, apparatus that is conventionally connected directly to a BTE unit, such as a headpiece or a power supply, may instead be connected to the BTE unit by way of the connectors (or other instrumentalities) associated with the case. Other cases in accordance with the present inventions allow a headpiece to be directly coupled to a BTE unit. In either case, parents of infants and toddlers, as well as adults who enjoy switching from a BTE unit to a body worn unit and back, can obtain a BTE unit and a case instead of the considerably more expensive combination of a BTE unit and a body worn unit without any reduction in functionality.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments of the inventions will be made with reference to the accompanying drawings.

FIG. 3A is a flow chart illustrating a method in accordance with one embodiment of a present invention.

FIG. 7 is perspective view of a speech processor case in accordance with one embodiment of a present invention in a closed orientation.

FIG. 8 is perspective view of the speech processor case illustrated in FIG. 7 in an open orientation.

FIG. 9 is perspective view of the speech processor case illustrated in FIG. 7 with the power supply cover in an open orientation.

FIG. 14 is perspective view of a speech processor case in accordance with one embodiment of a present invention in a closed orientation.

FIG. 15 is perspective view of the speech processor case illustrated in FIG. 14 in an open orientation.

FIG. 17 is a plan view of a speech processor case in accordance with one embodiment of a present invention in an open orientation.

FIG. 18 is an end view of the speech processor case illustrated in FIG. 17 in a closed orientation.

FIG. 19 is a side view of the speech processor case illustrated in FIG. 17 in a closed orientation.

FIG. 20 is a cutaway view of the speech processor case illustrated in FIG. 17 in a closed orientation with a speech processor unit therein.

FIG. 21 is a cutaway view of a speech processor case in accordance with one embodiment of a present invention in a closed orientation with a speech processor unit therein.

FIG. 22 is a side view of a speech processor case in accordance with one embodiment of a present invention in an open orientation.

FIG. 23 is a side view of the speech processor case illustrated in FIG. 22 in a closed orientation.

FIG. 24 is a side view of the speech processor case illustrated in FIG. 22 in a closed orientation with a speech processor unit therein.

FIG. 34 is a top view of the power portion of the speech processor case illustrated in FIG. 31.

FIG. 35 is a bottom view of the main portion of the speech processor case illustrated in FIG. 31.

FIG. 36 is a bottom view of the control portion of the speech processor case illustrated in FIG. 31.

FIG. 37 is a top view of the main portion of the speech processor case illustrated in FIG. 31.

FIG. 40 is a section view of a headpiece connector that may be employed in the speech processor case illustrated in FIG. 31.

FIG. 41 is an exploded view on an exemplary speech processor and speech processor power supply.

FIG. 42 is a plan view of the power/data connector of the exemplary speech processor illustrated in FIG. 41.

FIG. 43 is a plan view of the power/data connector of the exemplary speech processor case illustrated in FIG. 31.

FIGS. 44-46 are front views showing the docking of the speech processor illustrated in FIG. 41 within the speech processor case illustrated in FIG. 31.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions. The detailed description is organized as follows:

I. Exemplary Speech Processors
II. Exemplary Speech Processor Cases

The section titles and overall organization of the present detailed description are for the purpose of convenience only and are not intended to limit the present inventions.

The present inventions have application in a wide variety of systems that provide sound (i.e. either sound or a perception of sound) to the hearing impaired as well as others who require such systems on a situational basis. One example of such a system is an ICS system where an external speech processor communicates with a cochlear implant and, accordingly, the present inventions are discussed in the context of ICS systems. The present inventions are not, however, limited to ICS systems and may be used in combination with other systems for the hearing impaired that currently exist, or are yet to be developed. For example, the present inventions are applicable to behind-the-ear "hearing aid" units that include digital signal processors.

I. Exemplary Speech Processor Units

Figure 1:
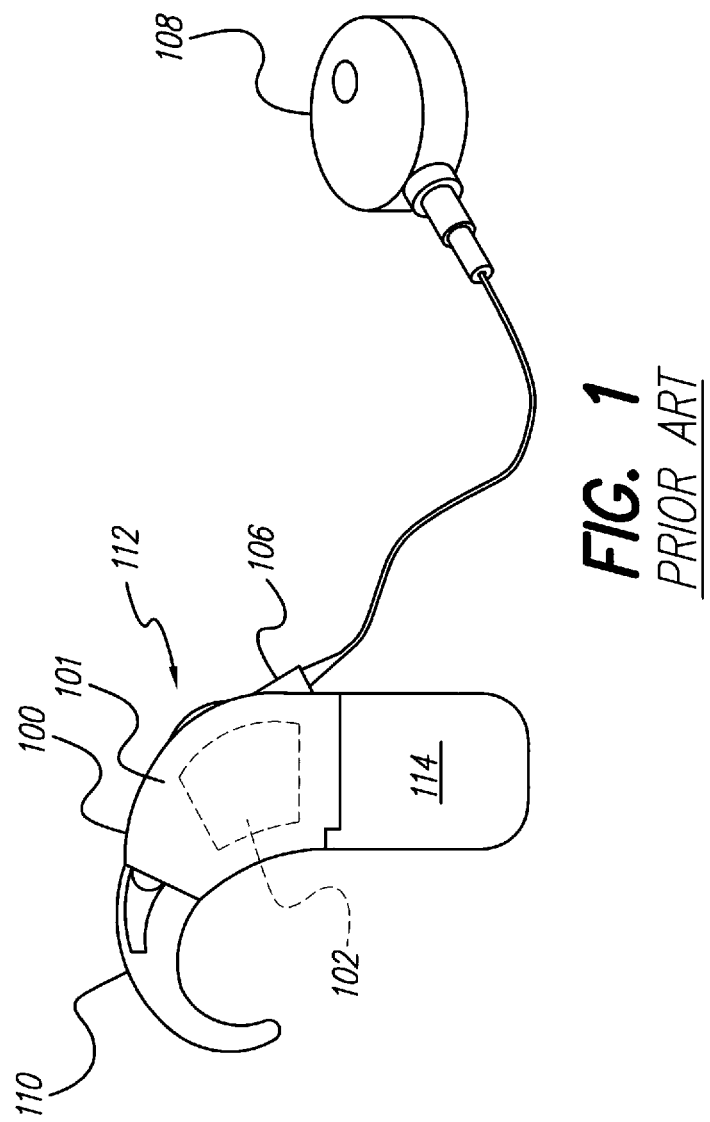
FIG. 1 is a perspective view of a conventional BTE unit and associated structures.
Figure 2:
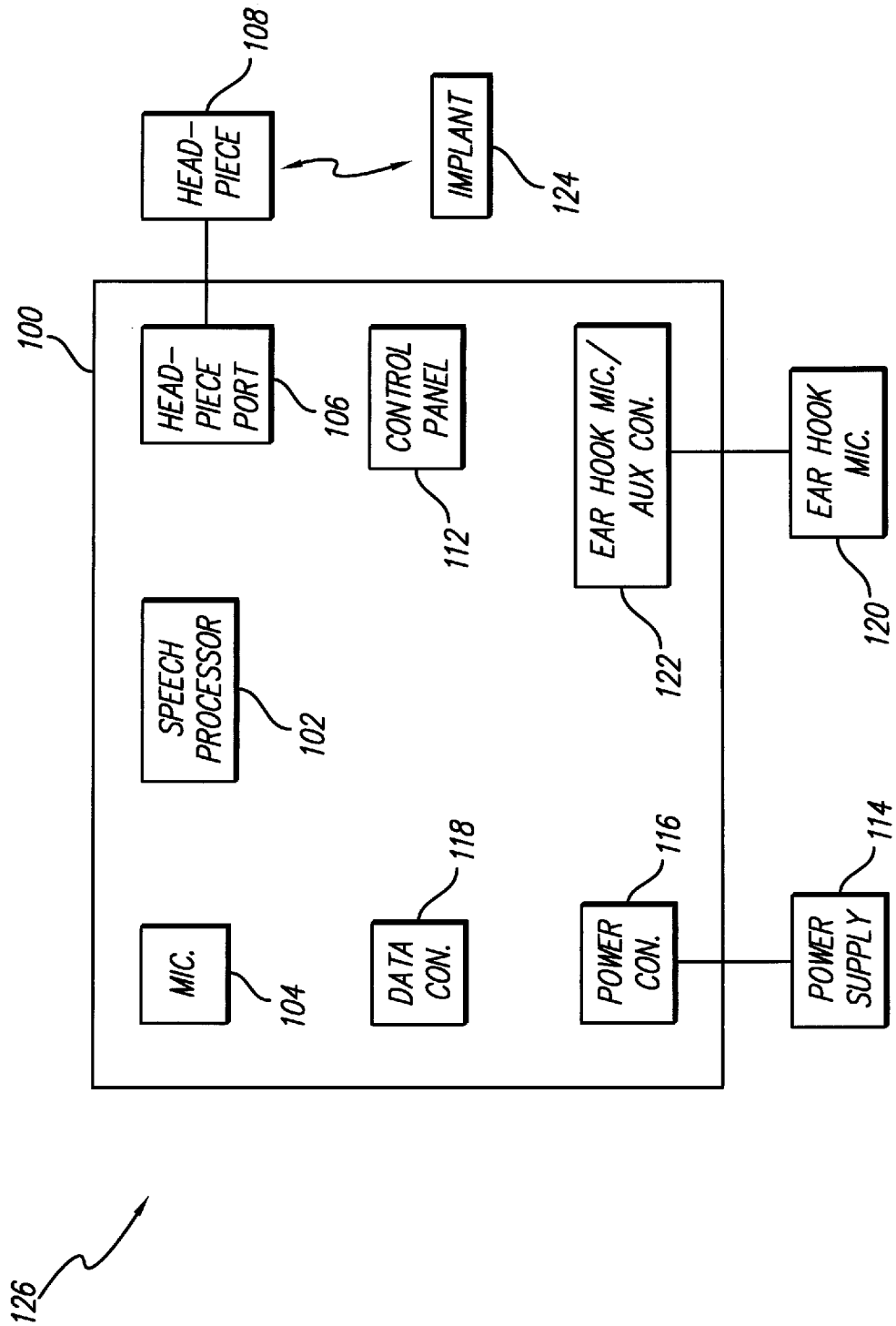
FIG. 2 is functional block diagram of an ICS system including the conventional BTE unit illustrated in FIG. 1.

One example of a speech processor unit which may be used in combination with, or form part of, the present inventions is the conventional BTE unit 100 illustrated in FIGS. 1 and 2. The BTE unit 100 includes an external housing 101, a speech processor 102 located within the external housing, an on-board microphone 104, a headpiece port 106 that allows the BTE unit to be connected to a headpiece 108, an ear hook 110, and a control panel 112. As used herein, the term "port" represents any and all suitable "male" or "female" electrical and/or electromechanical connector or other device which facilitates the communication between two devices. The exemplary control panel 112 includes a volume knob and a program switch. The BTE unit 100 is powered by a removable power supply 114 and, to that end, the BTE unit includes a power connector 116 in addition to a suitable mechanical connector for securing the power supply to the BTE unit. Suitable power supplies include rechargeable and disposable batteries or other electrochemical cells. One or more data connectors 118 are also provided. Such connectors may be used, for example, to connect the BTE unit 100 to a clinician's programming interface (CPI) unit, a clinician's fitting station, and/or other external devices in order to, for example, test and reprogram the operational parameters of the speech processor 102 and/or transfer a set of stimulation parameters directly to a speech processor unit. Finally, an additional microphone 120 may be mounted on the ear hook 110 and the exemplary BTE unit 100 includes a connector 122 for the ear hook microphone and/or an auxiliary device such as a mobile phone or a music player. The BTE unit 100 can be programmed to process sounds received by way of the on-board microphone 104, the ear hook microphone/auxiliary device connector 122, or some blend of the two.

During use, ambient sound pressure waves picked up by the on-board microphone 104, the ear hook microphone 120, and/or received from an auxiliary device are converted into electrical signals. The electrical signals are then processed by the speech processor 102, converted into a pulse sequence having varying pulse widths and/or amplitudes, and transmitted through the headpiece 108 to a receiver circuit in the implant 124. The implant 124 also includes an electrode array that is inserted into the cochlea of the inner ear. The electrical stimulation current generated by the implant is applied to varying electrode combinations to create a perception of sound. The BTE unit 100, headpiece 108 and implant 124 together define an ICS system 126.

Other exemplary BTE units are described below with reference to FIGS. 25-47.

Although the present inventions are not limited to any particular BTE units or ICS systems, commercially available examples of suitable BTE units include the HIRES™ AURIA™ BTE unit and the HARMONY BTE unit from Advanced Bionics, LLC in Valencia, Calif. The present inventions are also not limited to BTE units that communicate with the implant by way of a headpiece. For example, BTE units that wirelessly communicate with the implant (i.e. without a headpiece and associated cable) may also be employed.

II. Exemplary Speech Processor Cases

Figure 3:
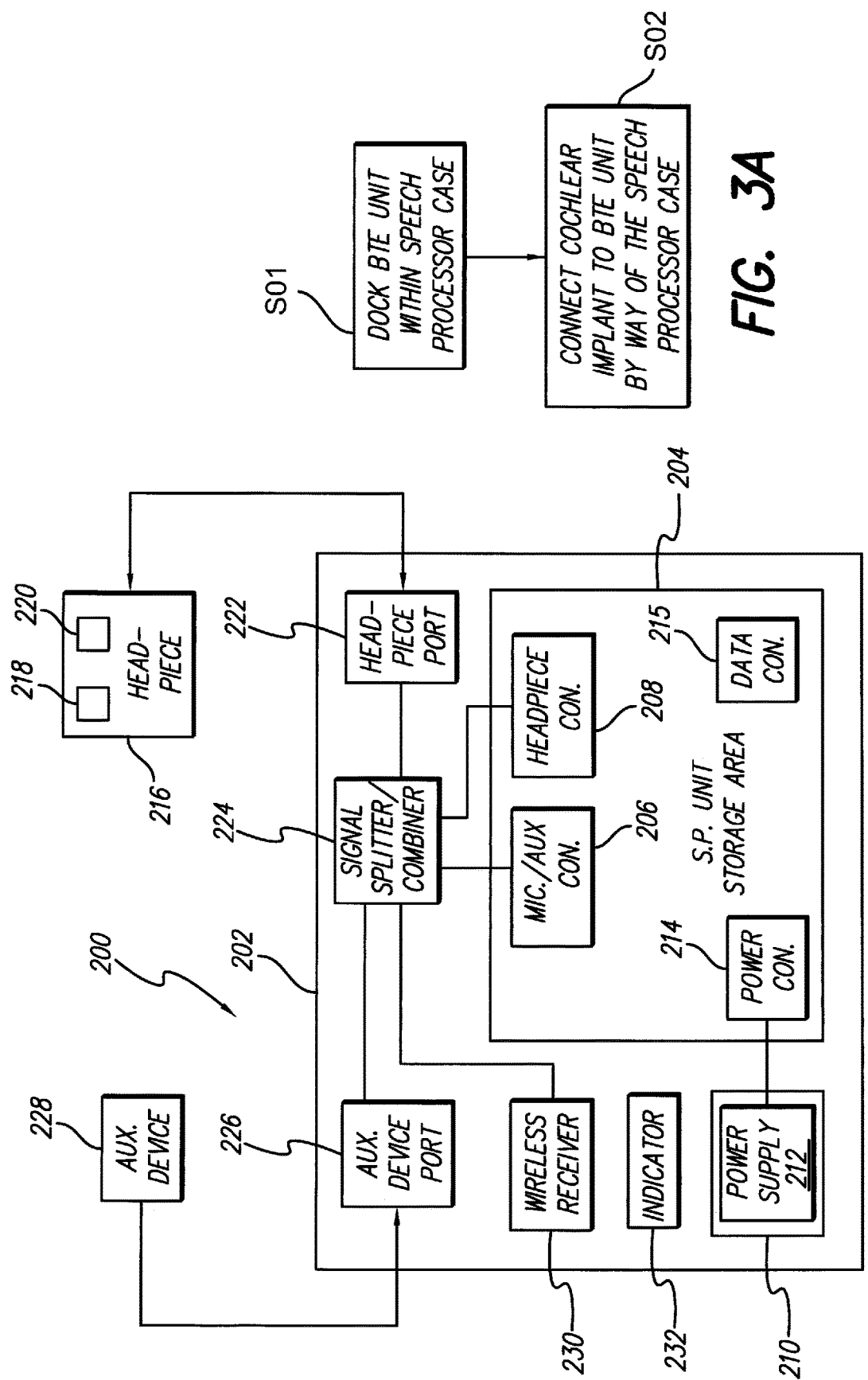
FIG. 3 is a functional block diagram of a speech processor case, a headpiece and an auxiliary device in accordance with one embodiment of a present invention.

FIG. 3 is a functional block diagram of a speech processor case (or "case") 200 with certain components that can be found in speech processor cases in accordance with many embodiments of the present inventions. Such a case may be used to store a conventional speech processor unit, such as a BTE unit, in such a manner that the case and BTE unit together form a body worn speech processor unit. Accordingly, the case allows a conventional BTE unit to function as a body worn unit as well as a BTE unit, which is also referred to herein as "converting" a BTE unit into a body worn unit or "docking" a BTE unit within a case. Additionally, although various cases are discussed in combination with the exemplary BTE unit 100 illustrated in FIGS. 1 and 2, the present inventions are not limited to any particular behind-the-ear units.

Referring more specifically to FIG. 3, the exemplary speech processor case 200 includes a housing 202 with a storage area 204 for a BTE unit, such as the BTE unit 100, or other speech processor unit. A plurality of connectors are associated with the storage area 204. The storage area and connectors associated therewith together define a BTE docking station. With respect to the connectors themselves, the case 200 is provided with a microphone/auxiliary device connector 206, which may be connected to the BTE unit ear hook microphone/auxiliary device connector 122, as well as a headpiece connector 208, which may be connected to the BTE headpiece port 106. The case 200 may also be provided with a power supply receptacle 210 for a power supply 212, such as disposable or rechargeable battery or other electrochemical cell, which may be used to power the BTE unit 100 when it is located within the case. To that end, the case 200 is provided with a power connector 214 that connects the power supply 212 to the BTE unit power connector 116, typically by way of electrical contacts associated with the power supply receptacle 210. The power supply 212 may also be used to power those aspects of the case 200 that require power. Additionally, in some instances, one or more data connectors 215 may be provided to couple the case 200 to the BTE unit data connector(s) 118.

The BTE microphone 104 will be located within the speech processor case 200 during use. As such, the exemplary case 200 may be used in combination with a headpiece 216 that, in addition to the circuitry 218 which communicates with the cochlear implant, also includes a microphone 220 that is used to pick up the ambient sound pressure waves. The headpiece 216 may be connected to the case microphone/auxiliary device connector 206 (and, therefore, the BTE unit ear hook microphone/auxiliary device connector 122) as well as to the headpiece connector 208 (and, therefore, to the BTE unit headpiece port 106) by way of a headpiece port 222 and a signal splitter/combiner 224. The signal splitter/combiner 224 demodulates the RF headpiece signal, which is modulated by the microphone signal, and also combines audio signals received by way of the headpiece port 222 and the auxiliary device port 226. A suitable signal splitter/combiner is the signal splitter/combiner found in the Platinum Signal Processor body worn unit from Advanced Bionics Corporation. The signal splitter/combiner 224 also allows the signals to the implant communication circuitry 218 to reach only the headpiece connector 208, and signals from the headpiece microphone 220 to reach only the microphone connector/auxiliary device connector 206. The exemplary case 200 is also provided with an auxiliary device port 226 that allows an auxiliary device (e.g. a mobile phone, digital music player or the like) to be connected to the BTE unit 100 by way of the microphone connector/auxiliary device connector 206 and signal splitter/combiner 224.

It should also be noted here that the above-described functionality of the splitter/combiner may instead be incorporated into the speech processor 102 of the BTE unit 100 as well as the speech processors of other BTE units (such as those described below).

The exemplary speech processor case 200 may also be provided with a wireless transceiver 230 such as, for example, an FM transceiver that allows wirelessly transmitted audio signals to be received by the BTE unit 100. Such transceivers allow students to receive wireless audio signals from a teacher who wears a wireless transmitter during class. The wireless transceiver 230 also allows the BTE unit 100 to transmit signals to a remote receiver. Such signals include status signals (e.g. a low battery signal to the teacher) and signals to an implantable device in those instances where there is no headpiece and the BTE unit transmits signals directly to the implantable device.

One or more audible, visible and/or otherwise perceptible indicator devices 232, such as a speaker or buzzer, an LED or other light source and/or a vibrator, may also be incorporated into the case 200. Such indicator devices 232 may be used to provide and audible, visible and/or otherwise perceptible indication as to the status of components of the BTE unit 100 and/or the case 200. Such indications may be provided when, for example, the power supply 212 is almost fully depleted, the BTE unit 100 is not properly docked within the case 200, or the headpiece 216 is dislodged.

Turning to FIG. 3A, some of the methods by which the speech processor cases disclosed herein may be used to allow a BTE unit to function as a body worn unit may briefly be summarized as follows. First, in Step S01, the BTE unit is docked within the speech processor case. Next, in Step S02, the cochlear implant is coupled to the BTE unit by way of the speech processor case. In some instances, Step S02 may be accomplished in part by connecting a headpiece to the case.

Speech processor cases in accordance with the present inventions may be provided with additionally functionality. Such functionality is discussed below in the context of some of the illustrated embodiments.

Figure 4:
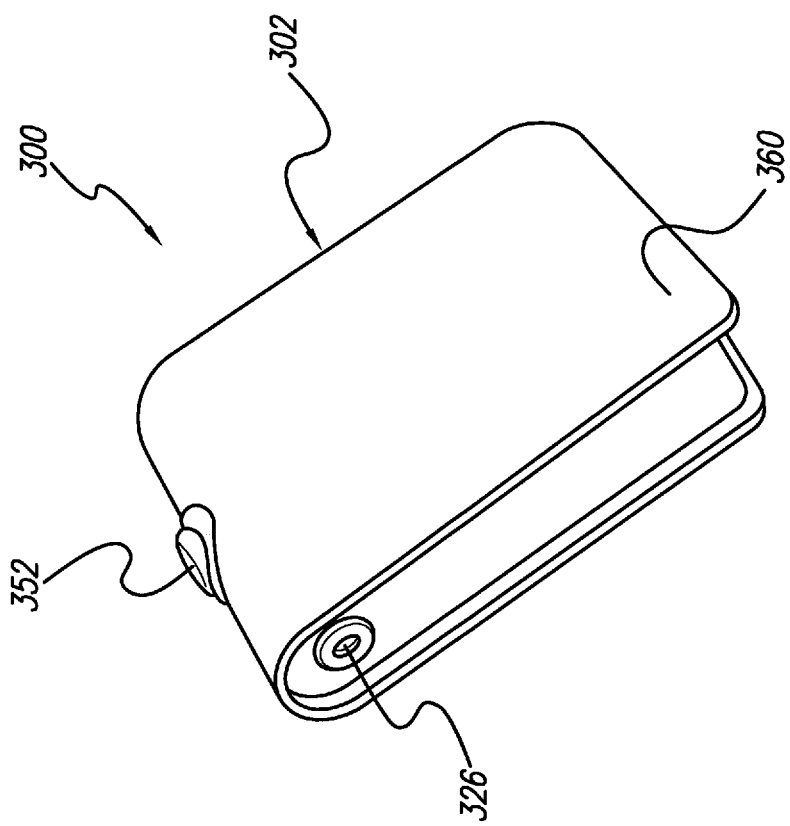
FIG. 4 is perspective view of a speech processor case in accordance with one embodiment of a present invention in a closed orientation.
Figure 5:
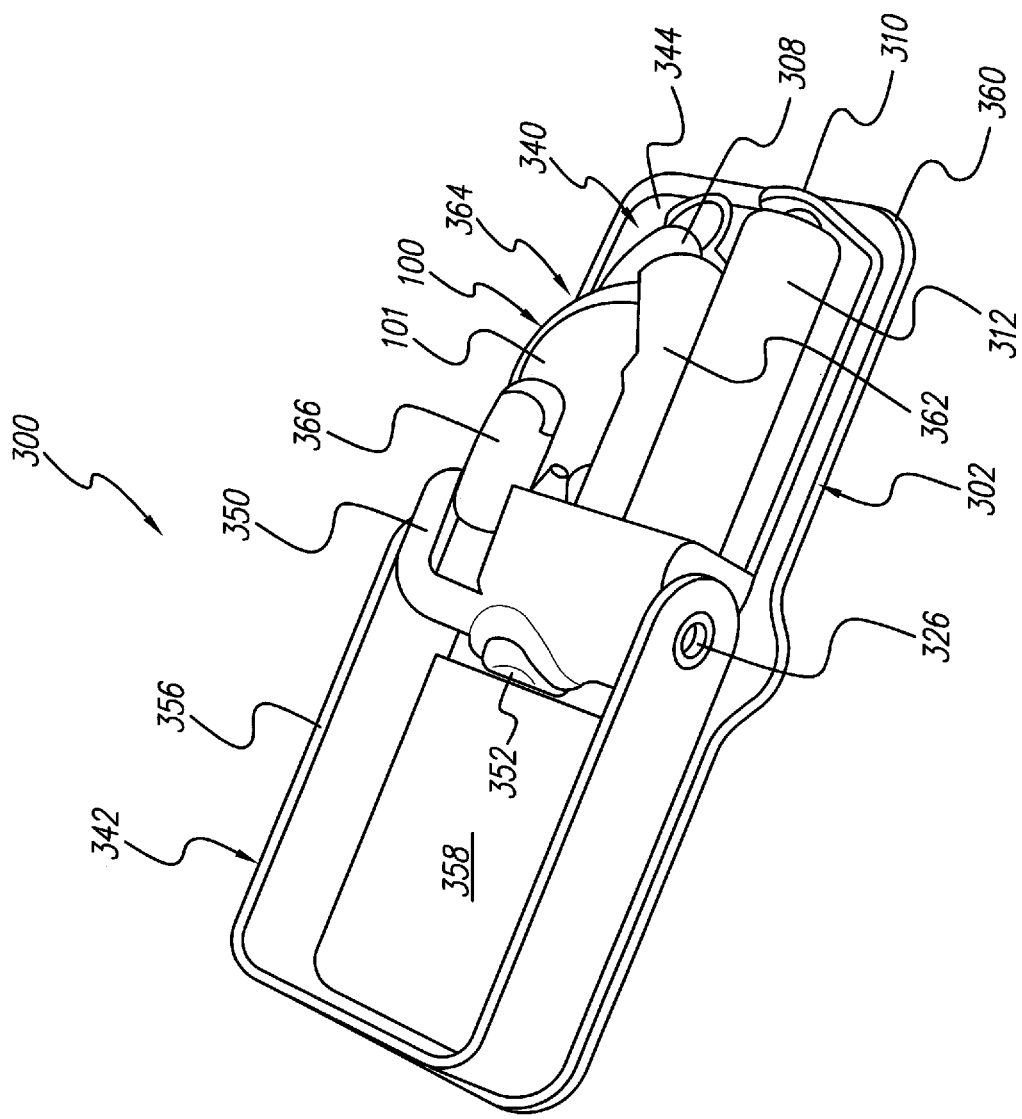
FIG. 5 is perspective view of the speech processor case illustrated in FIG. 4 in an open orientation.
Figure 6:
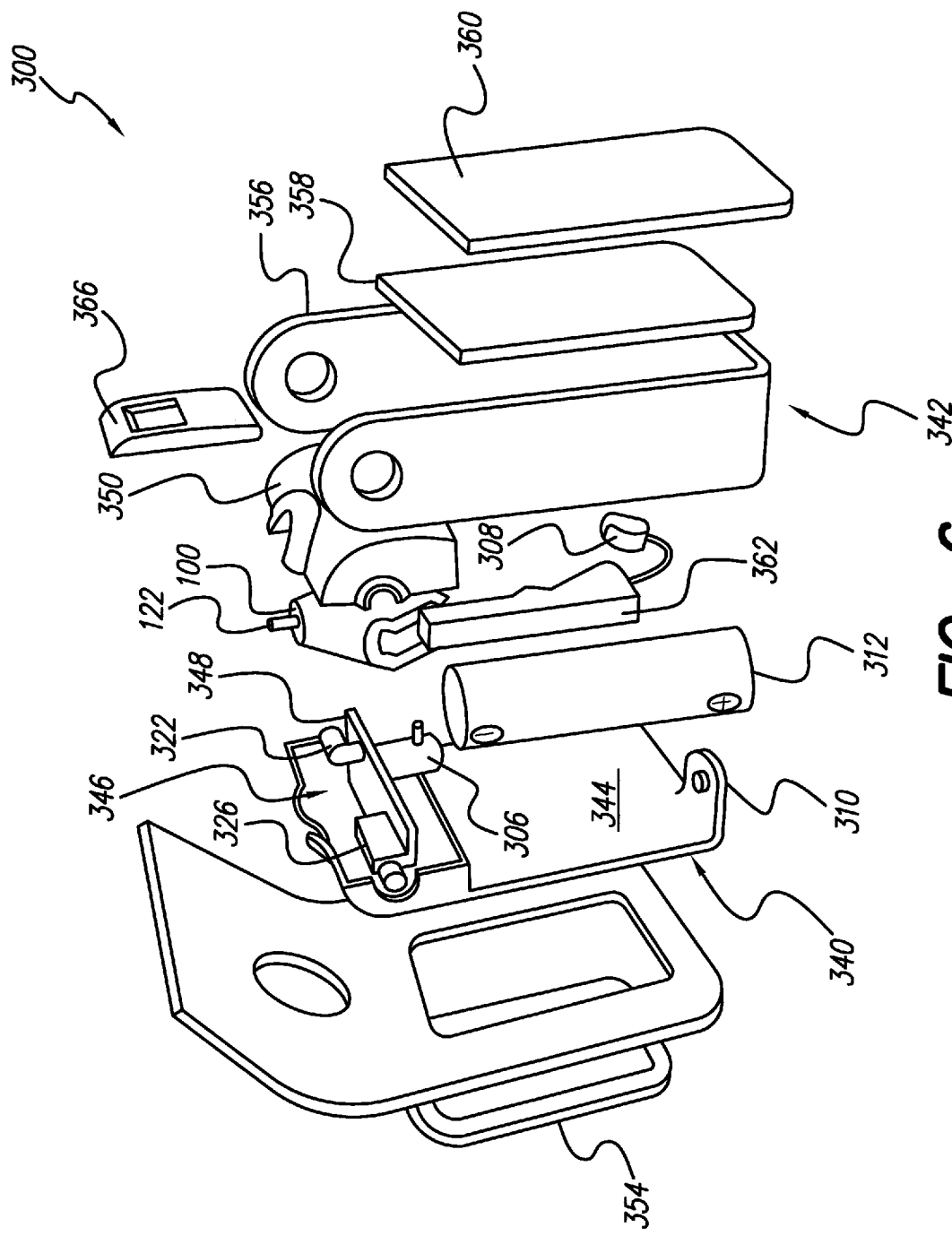
FIG. 6 is an exploded view of the speech processor case illustrated in FIG. 4.
Figure 10:
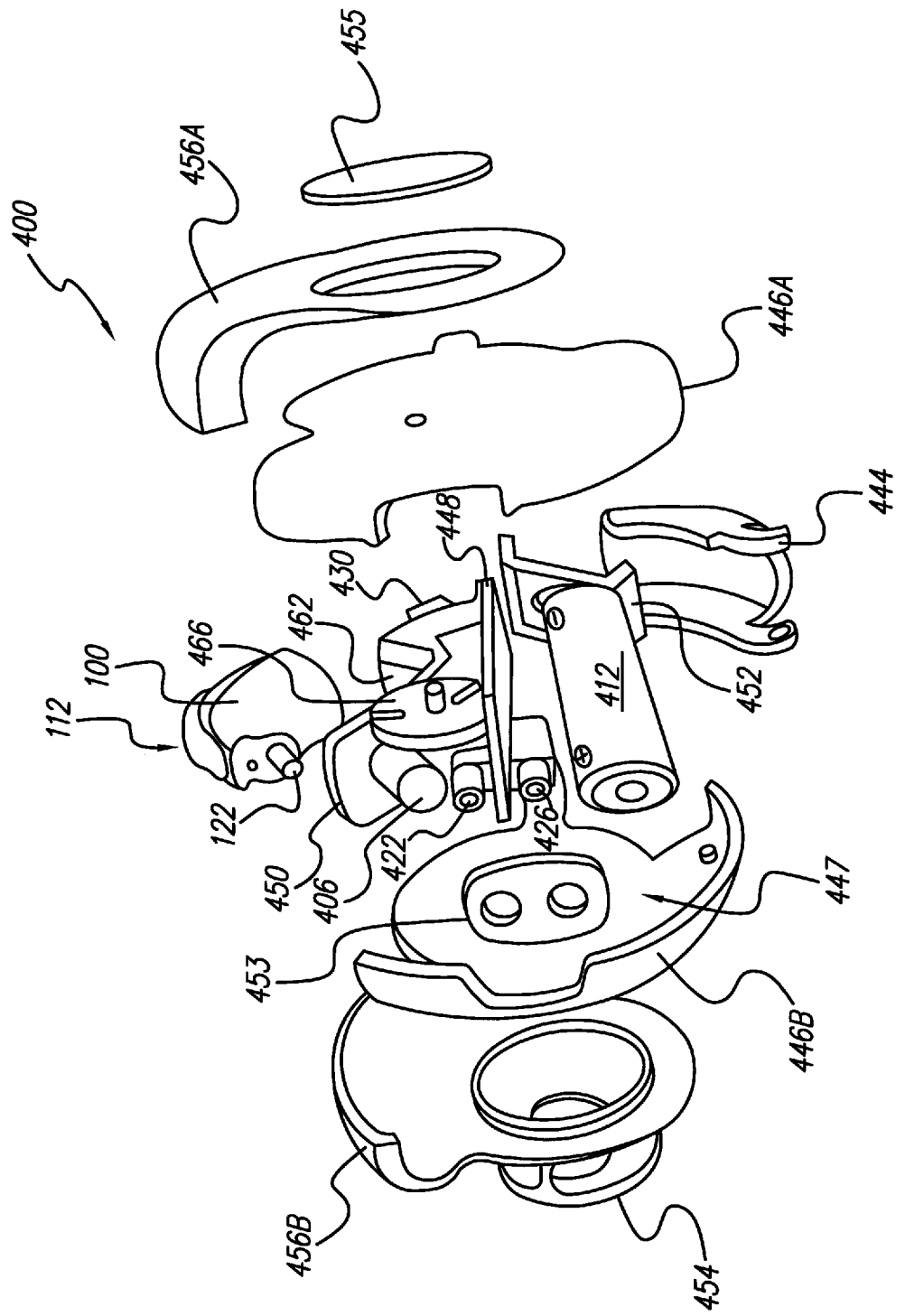
FIG. 10 is an exploded view of the speech processor case illustrated in FIG. 7.

The exemplary speech processor case 300 illustrated in FIGS. 4-6 may include some or all of the functional components discussed above in the context of FIG. 3 and similar functional components are represented by similar reference numerals. Referring first to the housing, the exemplary housing 302 includes a housing base member 340 and a housing cover 342 that is pivotable relative to the housing base member. The base member 340 includes a main portion 344, which defines a open region 346 for a circuit board 348, and a board cover 350. The circuit board 348 carries a case microphone/auxiliary device connector 306, a headpiece port 322, an auxiliary device port 326, and a signal splitter/combiner (not shown). The main portion 344 and board cover 350 together define four openings. Two of the openings facilitate access to the headpiece and auxiliary device ports 322 and 326, the microphone/auxiliary device connector 306 extends through one of the openings, and a volume control knob 352 extends through the final opening. The volume control knob 352 may be connected to an amplifier/attenuator on the circuit board 348 or, alternatively, may be connected to case data connector(s) 215 so that volume may be controlled at the BTE unit 100. A belt loop or clip 354, or other suitable mounting device (e.g. a lanyard ring or safety pin), is secured to the exterior of the main portion 344 and may be used to secure the case to the clothing or body of the user. With respect to power, the housing main portion 344 includes a power supply receptacle 310 for a battery or other power supply 312 (note FIGS. 5 and 6). The pivotable housing cover 342 consists of a U-shaped portion 356 and a flat portion 358 secured to the U-shaped portion. The U-shaped portion 356 also includes a pair of openings, which are aligned with two of the openings defined by the base member main portion 344 and board cover 350, to further facilitate access to the headpiece and auxiliary device ports 322 and 326.

The housing 302 is also provided with a user-changeable skin 360 which may be selectively secured to, or removed from, the housing for aesthetic purposes. A typical user would obtain a number of skins and cover the housing with the skin of his/her choice. The skin 360 may be attached to the housing base member main portion 344 and cover flat portion 358 though the use of snaps and other suitable instrumentalities. Exemplary materials for the skins include fabrics and plastics.

Turning to the manner in which the BTE unit 100 is docked within the exemplary case 300 illustrated in FIGS. 4-6, and connected to the various apparatus associated therewith, the case includes a guide rail 362 that can slidably receive the BTE unit when the case is in the open orientation illustrated in FIG. 5. As such, the area adjacent to the guide rail 362 defines the BTE storage area 364. The BTE unit 100 is inserted into the case 300 without the power supply 114. To that end, the guide rail 362 also includes a power connector (not shown) that is electrically connected to the power supply receptacle 310 and is positioned and configured such that it will mate with the BTE power connector 116. Data connectors (not shown), which are associated with the guide rail 362, may be provided in order to connect to the BTE unit data connectors 118.

With respect to the connectors that are not carried by the guide rail 362 in the exemplary case 300, a slider 366 may be used to connect the microphone/auxiliary device connector 306 to the BTE unit ear hook microphone/auxiliary device connector 122. The slider 366 will be in a retracted state while the BTE unit is inserted into, or removed from, the case 300. A headpiece connector 308, which is connected to the case headpiece port 322, may be plugged into the BTE unit headpiece port 106 when the BTE unit 100 is in the case 300.

After the connections are made, the BTE unit 100 and case 300 will together define a body worn speech processor unit that may, for example, be mounted on an infant harness or the clothing of an adult. A headpiece (such as the headpiece 216 illustrated in FIG. 3) may be connected to the body worn unit so that the body worn unit can be used in conventional fashion.

Another exemplary speech processor case is generally represented by reference numeral 400 in FIGS. 7-10. Case 400 may include some or all of the functional components discussed above in the context of FIGS. 3-6 and similar functional components are represented by similar reference numerals. Referring first to the housing, the exemplary housing 402 includes a housing base member 440, a processor cover 442 that is rotatable relative to the base member, and a power supply cover 444. The base member 440 is formed by two essentially identical side portions 446a/446b (FIG. 10) which together define an internal region 447 for a circuit board 448, a power supply receptacle (not shown) and a battery 412 or other power supply. The internal region 447 is closed by an upper cover 450, a lower cover 452, and a front cover 453. The circuit board 448 carries a case microphone/auxiliary device connector 406, a headpiece port 422, an auxiliary device port 426, and a signal splitter/combiner (not shown). The headpiece and auxiliary device ports 422 and 426 are accessible through openings in the front cover 453. A belt loop or clip 454, or other suitable mounting device, is secured to the exterior of the side portion 446b and a name plate 455 is secured to the side portion 446a. The processor cover 442 consists of two essentially identical side pieces 456a/456b that are respectively rotatably secured to the base member side portions 446a/446b by the belt loop 454 and name plate 455.

Turning to the manner in which the BTE unit 100 is docked within the exemplary case 400 illustrated in FIGS. 7-10, and connected to the various apparatus associated therewith, the case includes a guide rail 462 (FIG. 10) that can slidably receive the BTE unit when the processor cover 442 is in the open orientation (FIG. 8). The guide rail 462 is part of the upper cover 450 and the area between the upper cover and the inner surface of the processor cover 442 defines the BTE storage area 464. The BTE unit 100 is inserted into the case 400 without the power supply 114. To that end, the guide rail 462 also includes a power connector (not shown) that is electrically connected to the power supply 412 and is positioned and configured such that it will mate with the BTE power connector 116 and data connectors that will mate with the BTE unit data connectors 118.

As illustrated for example in FIG. 8, the BTE unit 100 is docked within the BTE storage area 464 such that the BTE control panel 112 is readily accessible when the processor cover 442 is moved to the open orientation. Additionally, in the illustrated embodiment, the belt loop 454 is oriented relative to the housing base member 440 such that the BTE control panel 112 will face upwardly when worn on a belt.

With respect to the connectors that are not carried by the guide rail 462 in the exemplary case 400, a cam 466 (FIG. 10) may be used to connect the microphone/auxiliary device connector 406 to the BTE unit ear hook microphone/auxiliary device connector 122. The cam 466, which is connected to the case microphone/auxiliary device connector 406 and is engaged by the processor cover 442 over the 10-20% portion of the processor cover's range of motion that is closest to the fully closed orientation, drives the case microphone/auxiliary device connector a short distance toward the BTE unit ear hook microphone/auxiliary device connector 122 as the processor cover is closed. The cam 466 also drives the case microphone/auxiliary device connector 406 the same short distance in the opposite direction as the processor cover 442 is opened. A headpiece connector 408, which is connected to the case headpiece port 422, may be plugged into the BTE unit headpiece port 106 after the BTE unit 100 is positioned on the guide rail 462.

The exemplary case 400 is also provided with a wireless transceiver 430, such as an FM module, that is removably mounted within the BTE storage area 464 and connected to a corresponding port (not shown). The addition of the wireless transceiver 430 will, for example, allow a student to receive wireless audio signals from a teacher who wears a wireless transmitter during class. The wireless transceiver 430 also allows the BTE unit 100 to transmit signals to a remote receiver. Such signals include status signals (e.g. a low battery signal to the teacher) and signals to an implantable device in those instances where there is no headpiece and the BTE unit transmits signals directly to the implantable device.

The exemplary case 400 may also be configured such that it is child resistant in order to prevent children from obtaining access to the BTE unit 100 and/or the power supply 412. This will typically be accomplished by including child resistant latching mechanisms (not shown) on the housing base member 440 and processor cover 442 and/or housing base member and the power supply cover 444. Additionally, although the processor cover 442 may be substantially transparent so that the user can observe the BTE unit 100, processor covers on cases intended for use with children are preferably opaque (as shown in FIGS. 7-10) in order to prevent the child from seeing the BTE unit. In such instances, the case will typically include certain audible/visible indicator devices (discussed above with reference to FIG. 3 and below with reference to FIGS. 14-16) so that a parent or teacher will be able to stay apprised of the status of the BTE unit 100 and battery 412.

After the connections within the case 400 are made, the BTE unit 100 and the case will together define a body worn speech processor unit that may, for example, be mounted on an infant harness or the clothing of an adult. A headpiece (such as the headpiece 216 illustrated in FIG. 3) may be connected to the body worn unit so that the body worn unit can be used in conventional fashion.

Figure 12:
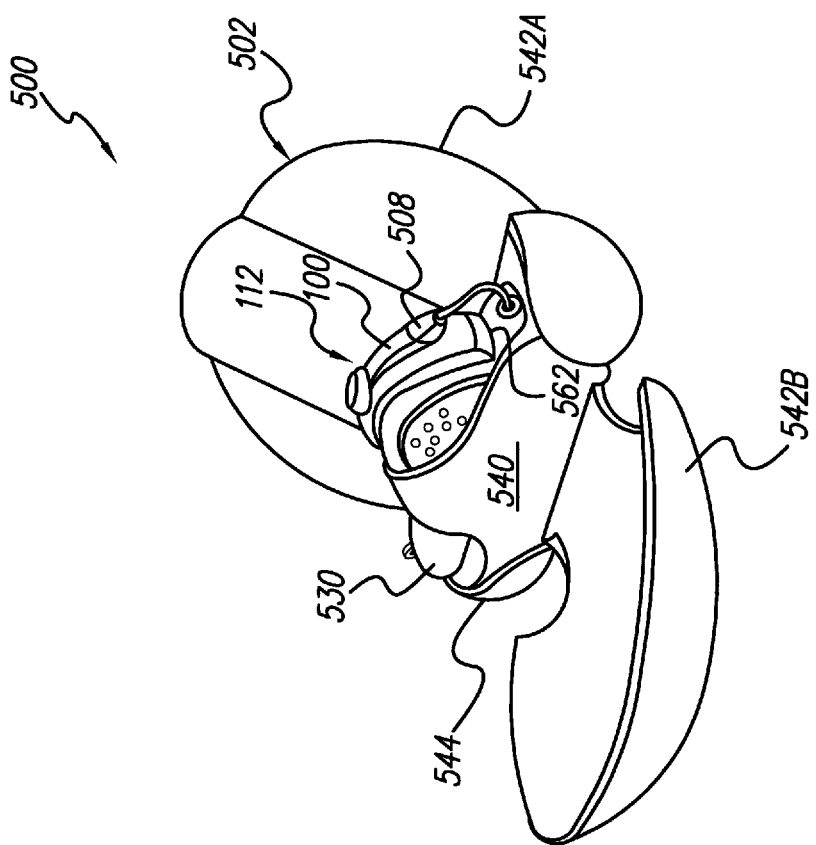
FIG. 12 is perspective view of the speech processor case illustrated in FIG. 11 in an open orientation.
Figure 11:
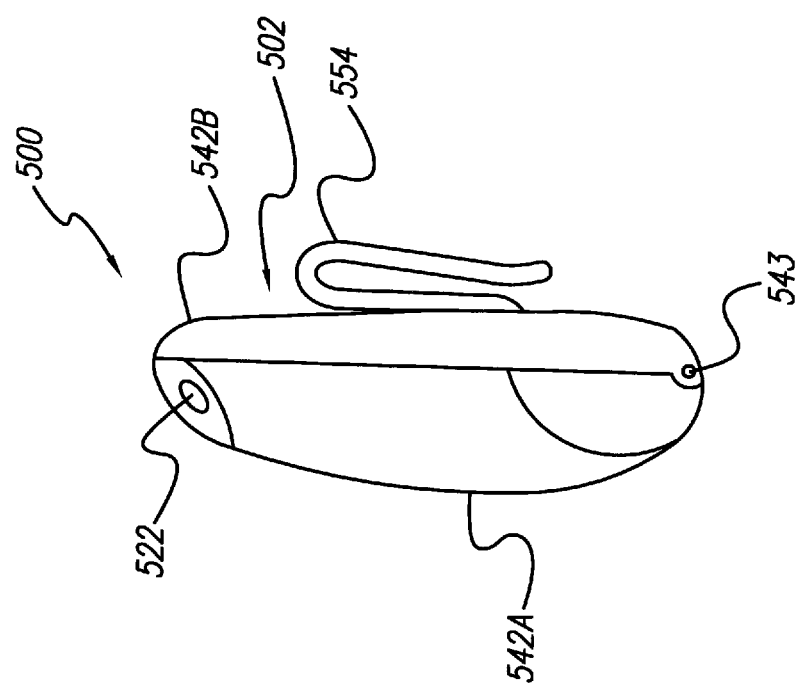
FIG. 11 is side view of a speech processor case in accordance with one embodiment of a present invention in a closed orientation.
Figure 13:
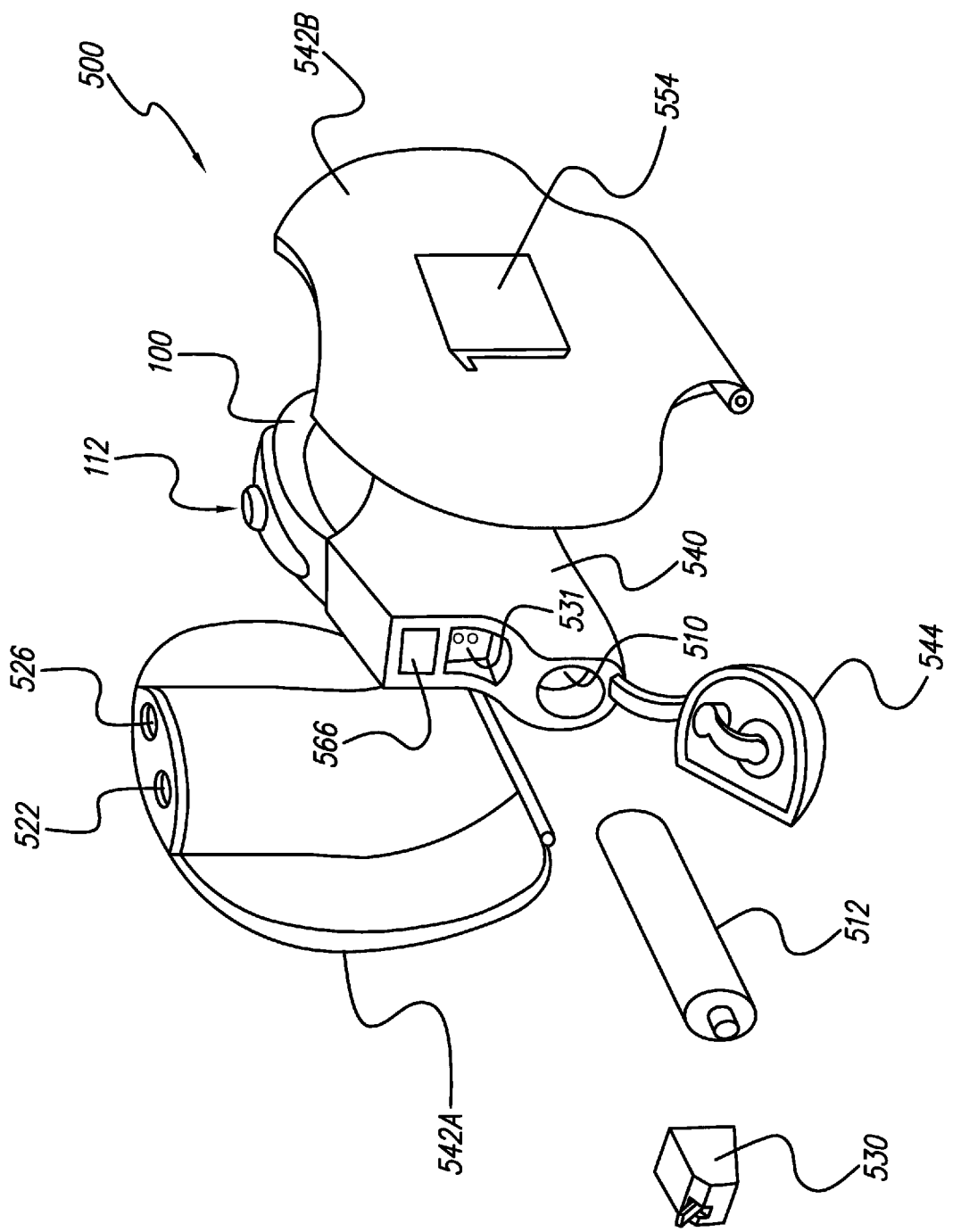
FIG. 13 is an exploded view of the speech processor case illustrated in FIG. 11.

Another exemplary speech processor case, which is generally represented by reference numeral 500 in FIGS. 11-13, may include some or all of the functional components discussed above in the context of FIGS. 3-10 and similar functional components are represented by similar reference numerals. Referring first to the housing, the exemplary housing 502 includes a BTE support portion 540 and a pair of covers 542a and 542b that are pivotably connected to the BTE support portion by a hinge 543. The BTE support portion 540 encloses a circuit board with a signal splitter/combiner (not shown), a case microphone/auxiliary device connector (also not shown), and a power supply receptacle 510 for a battery 512 or other suitable power supply. The power supply receptacle 510 is closed by a cover 544. The BTE support portion 540 also includes a port 531 for a wireless transceiver 530. The housing cover 542a carries a headpiece port 522 and an auxiliary device port 326, which are connected to the circuit board by way of, for example, a ribbon cable that extends though part of the hinge 543. A belt loop or clip 554, or other suitable mounting device, is secured to the exterior of the housing cover 542b.

The BTE unit 100 is docked within the exemplary case 500, and connected to various apparatus associated therewith, through the use of a guide rail 562 that slidably receives the BTE unit. The area between the guide rail 562 and the inner surfaces of the covers 542a and 542b defines the BTE storage area 564. The BTE unit 100 is inserted into the case 500 without the power supply 114 and the guide rail 562 includes a power connector (not shown) that is electrically connected to the power supply receptacle 510. The power connector is positioned and configured such that it will mate with the BTE power connector 116. Data connectors (not shown), which are associated with the guide rail 562, may be provided in order to connect to the BTE unit data connectors 118.

With respect to the connectors that are not carried by the guide rail 562 in the exemplary case 500, a button 566 may be used to connect the microphone/auxiliary device connector (not shown) to the BTE unit ear hook microphone/auxiliary device connector 122. The button 566 is preferably a spring biased button that alternately connects and disconnects the case microphone/auxiliary device connector and the BTE unit ear hook microphone/auxiliary device connector 122 when pressed. A headpiece connector 508, which is connected to the case headpiece port 522, may be plugged into the BTE unit headpiece port 106 when the BTE unit 100 is in the case 500.

After the connections are made, the BTE unit 100 and case 500 will together define a body worn speech processor unit that may, for example, be mounted on an infant harness or the clothing of an adult. A headpiece (such as the headpiece 216 illustrated in FIG. 3) may be connected to the body worn unit so that the body worn unit can be used in conventional fashion.

Figure 16:
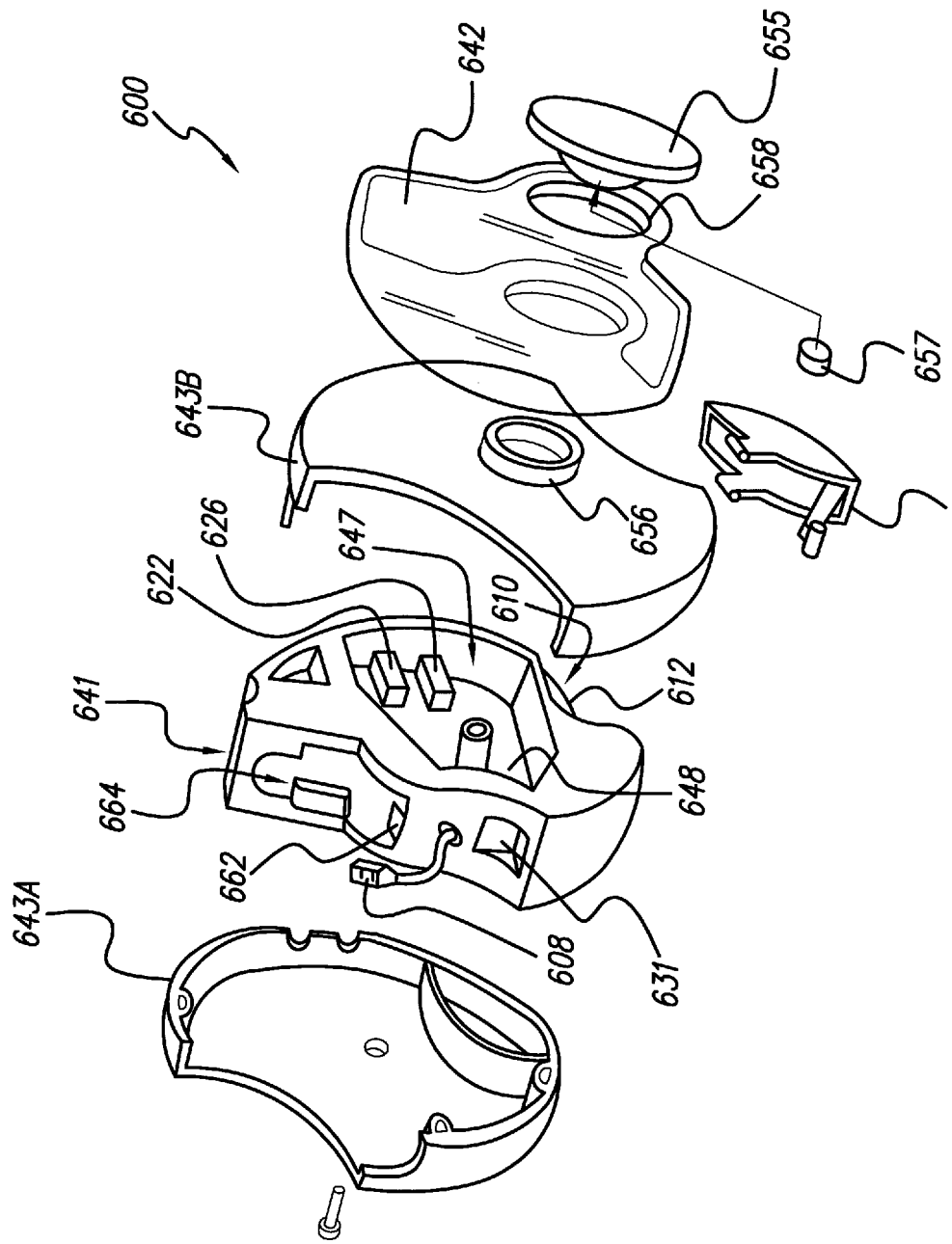
FIG. 16 is an exploded view of the speech processor case illustrated in FIG. 14.

Still another exemplary speech processor case, which is generally represented by reference numeral 600, is illustrated in FIGS. 14-16. Case 600 may include some or all of the functional components discussed above in the context of FIGS. 3-13 and similar functional components are represented by similar reference numerals. Referring first to the housing, the exemplary housing 602 includes a base member 640, a processor cover 642 that is rotatable relative to the base member, and a power supply cover 644. The housing base member 640 consists primarily of a center portion 641 and a pair of side portions 643a/643b. The center portion 641 defines an internal region 647 for a circuit board 648 as well as a power supply receptacle 610 for a battery 612 or other power supply. The base member internal region 647 is covered by the side portions 643a/643b. The circuit board 648 carries a headpiece port 622, an auxiliary device port 626, and a signal splitter/combiner (not shown). The headpiece and auxiliary device ports 422 and 426 are accessible through an opening in the center portion 641, which is covered by a resilient port cover 646. A belt loop or clip 654, or other suitable mounting device, is secured to the exterior of the side portion 643a and a name plate 655 is secured to the side portion 643b by a magnet 657. The processor cover 642 is rotatably mounted on housing base member 640. More specifically, the side portions 643a/643b each include a mounting ring 656 (only one visible) and the processor cover 642 includes a pair of corresponding apertures 658. The belt clip 654 and nameplate 655 hold the processor cover 642 in place.

With respect to the manner by which the BTE unit 100 is docked within the exemplary case 600 and connected to the various apparatus associated therewith, the case includes a guide rail 662 (FIG. 16) that can slidably receive the BTE unit when the case is in the open orientation (FIG. 15). The guide rail 662 is part of the base member center portion 641 and the area between the guide rail and the inner surface of the processor cover 642 defines the BTE storage area 664. The BTE unit 100 is inserted into the case 600 without the power supply 114 and the guide rail 662 also includes a power connector (not shown) that is electrically connected to the battery 612 and is positioned and configured such that it will mate with the BTE power connector 116 and data connectors (not shown) that will mate with the BTE unit data connectors 118. The case microphone/auxiliary device connector (not shown) is also supported on the base member center portion 641 in such a manner that it will mate with the BTE unit ear hook microphone/auxiliary device connector 122. A mechanism such as, for example, a cam similar to that described above with respect to FIGS. 7-10, may be provided in order to insure proper connection of the case and ear hook microphone/auxiliary device connectors. A headpiece connector 608, which is connected to the case headpiece port 622, may be plugged into the BTE unit headpiece port 106 after the BTE unit 100 is positioned on the guide rail 662. The exemplary case 600 is also provided with a wireless transceiver 630, such as an FM module, that is removably mounted within the BTE storage area 664 and connected to a corresponding port 631.

The exemplary case 600 is configured such that the BTE unit 100 is readily visible to the user. Referring more specifically to FIGS. 14 and 15, the belt loop 654 is oriented relative to the housing 602 such that the BTE control panel 112 will face upwardly when the case 600 is worn on a belt. The processor cover 642 is also substantially transparent so that the user can observe the BTE unit 100, its control panel 112 and any visible indicators, when the processor cover is in the closed orientation. The orientation of the BTE unit 100 within the storage area 664 also makes it easy to manipulate devices on BTE control panel 112 (e.g., the volume knob) when the processor cover 642 is in the open orientation.

Finally, the exemplary speech processor case 600 includes a visible indicator 632, such as an LED, which may be used to provide the status of components of the BTE unit 100 and/or the case 600. Such indications may be provided when, for example, the power supply 612 is almost fully depleted, the BTE unit 100 is not properly docked within the case 600, or the headpiece 216 is dislodged.

After the connections within the case 600 are made, the BTE unit 100 and the case will together define a body worn speech processor unit that may, for example, be mounted on an infant harness or the clothing of an adult. A headpiece (such as the headpiece 216 illustrated in FIG. 3) may be connected to the body worn unit so that the body worn unit can be used in conventional fashion.

Another exemplary speech processor case is generally represented by reference numeral 700 in FIGS. 17-20. Unlike the cases illustrated in FIGS. 3-16, the exemplary case 700 does not include the various ports, connectors and circuitry described above. Nor does the case 700 include its own power supply. Instead, the exemplary case 700 allows a headpiece to be directly coupled to the BTE unit 100. Power for the BTE unit 100 is supplied by the removable power supply 114.

Referring first to FIGS. 17-19, the case 700 consists of a housing 702 and a mounting device 704 that performs the function of securely holding the BTE unit 100 within the housing. The housing 702 includes a housing base member 740 and a housing cover 742 that is pivotable relative to the base member. In addition to carrying the mounting device 704 and a belt clip 754, the base member 740 includes a cable guide 744 that is discussed below with reference to FIG. 20. The housing cover 742 consists of a U-shaped portion 756 that is pivotably secured to the base member 740 by a hinge 750, and a flat portion 758 that is secured to the U-shaped portion. The U-shaped portion 756 includes an opening 780 that is adjacent to, and in line with, the cable guide 744 when the housing cover 742 is in the closed orientation. The opening 780 may, in some instances, include a resilient seal (not shown) that conforms to the headpiece cable when the housing 702 is closed and prevents moisture, dirt and/or dust from entering the housing through the opening. A user-changeable skin (not shown), such as that discussable with reference to FIGS. 4-6, may also be carried by the housing 702.

The mounting device 704 may be any suitable structure that holds the BTE unit 100 in place and, preferably, does so without blocking the control panel 112 so that the user can continue to access the control panel after the BTE unit is secured by the mounting device. The mounting device 704 in the illustrated embodiment includes a plurality of resilient members 705*a-d* (FIGS. 17 and 20) which have inner surfaces that together define a storage area 764 that corresponds to the shape of the exterior surface of the BTE unit 100 and power supply 114. The storage area 764 is preferably slightly smaller than the BTE unit 100 and power supply 114 so as to create an interference fit when the BTE unit and power supply are mounted therein. Other suitable mounting devices include, for example, one or more resilient straps or a guide rail. The housing cover 742 may also include a resilient pad 782 that is positioned and configured such that it will be aligned with the storage area 764 and engage the BTE unit 100 when the housing 702 is closed. The mounting device 704 may, as another alternative to the resilient members 705*a-d*, be in the form of a resilient pad that is positioned in such a manner that the BTE unit will be "sandwiched" between the resilient pads when the housing 702 is closed.

The BTE unit 100 may be connected to a headpiece 216' and mounted within the exemplary case 700 in the manner illustrated in FIG. 20. The headpiece 216' is similar to the headpiece 216 illustrated in FIG. 3 in that the headpiece 216' has circuitry that communicates with a cochlear implant and a microphone that picks up ambient sound pressure waves. Here, however, the headpiece signal is not modulated by the microphone signal and, instead, the headpiece and microphone signals are carried by separate wires within a headpiece cable 234. The end of the cable 234 opposite the headpiece 216' splits into two parts. The portion with the wire(s) that carry the headpiece signal is coupled to the BTE unit headpiece port 106 by a connector 236, while the portion with the wire(s) that carry the microphone signal is coupled to the BTE unit ear hook microphone/auxiliary device connector 122 (visible in FIG. 6) by a connector 238.

It should also be noted that, in those instances where the case 700 is intended to be used with a speech processor that is capable of wirelessly communicating with the headpiece, the cable guide 744 and opening 780 may be omitted.

The BTE unit 100 and case 700 together define a body worn speech processor unit that may, for example, be mounted on an infant harness or the clothing of an adult. The body worn unit may be assembled by securing the BTE unit within the housing 702 with the mounting device 704. The headpiece cable 234, which may be connected to the BTE unit 100 before or after the BTE unit is secured to the mounting device 704, may then be positioned in the cable guide 744 so that the cable 234 will extend though the opening 780 to the headpiece 216' when the cover 742 is closed.

As illustrated for example in FIG. 21, the exemplary speech processor case 700 may also be used in conjunction with a headpiece 216" that is connected to the BTE unit 100 by way of the BTE unit data connectors 118 (note FIG. 2). The headpiece 216", which includes a microphone as well as circuitry that communicates with a cochlear implant, is connected to the BTE unit 100 by way of a cable 240 and a connector 242. The headpiece and microphone signals are carried by separate wires within the headpiece cable 240, and the connector 242 couples the wires to the appropriate BTE data connectors 118. With respect to power, the connector 242 is also configured to couple the power supply 114 to the BTE unit power connector 116 (note FIG. 2).

Another exemplary speech processor case is illustrated in FIGS. 22-24. The speech processor case 800 is similar to the case illustrated in FIGS. 17-20 in that it does not include the ports, connectors and circuitry described above with reference to FIGS. 3-16. Case 800 is, however, configured to store an on-board power supply that powers the BTE unit 100 in essentially the same manner as the case 600.

The exemplary housing 802 is similar to the housing 602 (FIGS. 14-16) in that the housing 802 includes a base member 840, a processor cover 842 that is rotatable relative to the base member, and a power supply cover 844. The base member 840 includes a power supply receptacle (not shown) for a battery or other power supply (not shown). A belt loop or clip 854, or other suitable mounting device, is secured to the exterior of the housing 802. The case 800 is also provided with a guide rail 862 that can slidably receive the BTE unit 100 and securely mount the BTE unit within the case. The area between the guide rail 862 and the inner surface of the processor cover 842 defines the BTE storage area 864 (FIG. 23). The guide rail 862 also includes a power connector (not shown) that is electrically connected to the case power supply and is positioned and configured such that it will mate with the BTE power connector 116 (FIG. 2) when the BTE unit 100 is mounted within the case 800.

The exemplary case 800 is configured such that the BTE unit 100 is readily visible to the user. More specifically, the belt loop 854 is oriented relative to the housing 802 such that the BTE control panel 112 will face upwardly when the case 800 is worn on a belt. The processor cover 842 is also substantially transparent so that the user can observe the BTE unit 100, its control panel 112 and any visible indicators, when the processor cover is in the closed orientation. The orientation of the BTE unit 100 also makes it easy to manipulate devices on BTE control panel 112 (e.g., the volume knob) when the processor cover 842 is in the open orientation.

The BTE unit 100 may be connected to a headpiece 216' in the manner described above with reference to FIG. 20. More specifically, the wire(s) in the cable 234 that carry the microphone signal are coupled to the BTE unit ear hook microphone/auxiliary device connector by a connector 238, and the wire(s) that carry the headpiece signal are coupled to the BTE unit headpiece port 106 by a connector 236. The base member 840 may include a cable slot 845 that allows the processor cover 842 to close without damaging the cable 234 (note FIG. 24). A similar slot may alternatively, or in addition, be formed in the processor cover 842. However, in those instances where the case 800 is intended to be used with a speech processor that is capable of wirelessly communicating with the headpiece, the slot(s) may be omitted.

After the BTE unit 100 is mounted within the case 800, the BTE unit and case will together define a body worn speech processor unit that may, for example, be mounted on an infant harness or the clothing of an adult.

With respect to materials and dimensions, cases in accordance with the present inventions may be formed from any suitable metal or plastic materials. The dimensions will typically depend on the dimensions of the speech processor unit intended to be docked therein. For example, a case intended for use with BTE units would typically be about 50-100 mm long, about 50-100 mm wide and about 20-30 mm thick. However, the size may be increased as needed in order to, for example, provide additional case functionality.

The speech processor cases described above with reference to FIGS. 3-24 may include a wide variety of additional devices that provide additional functionality and/or augment existing functionality. For example, the speech processor case power supply may be used to charge the BTE unit 100 removable power supply 114 while the BTE unit is used in combination with the case. This may be accomplished by providing a physical connector, either within the case or on the case exterior, or an inductive current connection (e.g., 27 MHz).

Speech processor cases in accordance with the present inventions may be provided with a circuitry that works in conjunction with the speech processor 102 to augment the speech processing functionality of the BTE unit or facilitates operation of the BTE unit within the case. Various examples of such cases are summarized in the following paragraphs and are described in detail below with reference to FIGS. 25-29. In some instances, the case circuitry may be configured to provide the basic functions necessary for a patient to hear should the BTE speech processor cease normal functioning.

Speech processor cases in accordance with the present inventions may also include communications electronics capable of wirelessly or directly (through wire, cable, or direct electrical contact) connecting the BTE unit 100 with external devices in addition to the aforementioned headpieces and implants. Such communications electronics (e.g., an ITEL communications microchip) may be used to, for example, establish a communication link with a clinician's programming interface unit, a clinician's fitting station, and/or other external devices. Accordingly, the communication electronics may facilitate the transfer of information and/or power to and from the case and the external devices. In those instances where a cable is employed, the cable may be manually wrapped and placed within a cable receptacle within the case. Such a cable receptacle may, alternatively, include a spring-loaded reel, or equivalent structure, capable of winding and/or retracting the cable into the case.

Speech processor cases in accordance with the present inventions may be provided with an antenna coil, or equivalent structure, that receives power through an inductive link from an external source. The power received may be used to power the operations of the case and/or charge the case's on-board power supply.

In addition the to the aforementioned volume control knob, speech processor cases in accordance with the present inventions may include exterior actuators (e.g. buttons, wheels, switches, etc.) capable of modifying various operational parameters of the BTE unit such as power, stimulation program selection, sensitivity, and other parameters. For example, a portion of the housing (e.g. the processor cover) may be provided with a rotatable wheel actuator that is physically connected to the BTE volume control knob or a button that is positioned and configured to make physical contact with a button on the BTE unit.

Speech processor cases in accordance with the present inventions may also include a display, such as a liquid crystal display, that can function as a status indicator and/or a control for the case. The display may be used to display text and/or graphics and may be accompanied by actuators or controls that permit a user to control operations of the case and/or the docked BTE unit. Such actuators or controls may also be used to prepare and send a program defining at least one set of stimulation parameters from the case to the BTE unit.

Speech processor cases in accordance with the present inventions may be provided with a wireless headpiece port that wirelessly (e.g. via radiofrequency link) connects the BTE unit to the headpiece. Accordingly, references herein to "headpiece connectors" include wireless connectors as well as connectors that require cable that runs from the case to the headpiece and the connections associated therewith included wireless and wired connections.

Speech processor cases in accordance with the present inventions may be configured to protect the BTE unit stored therein from wind, moisture, dirt, dust, and detrimental physical contact. This may be accomplished by providing water-tight seals, extra padding, and/or employing hard and soft polymers as appropriate.

Speech processor cases in accordance with the present inventions may include an external, on-board microphone that picks up ambient sound pressure waves and is used in conjunction with, or instead of, the headpiece microphone 220. The case microphone may be protected from the elements (e.g., wind and water) by a wind and water resistant cover that permits sound to pass there through without substantially changing the shape of the sound waves. Such a cover may include micro-holes or be a mesh or net-type cover.

Figure 25:
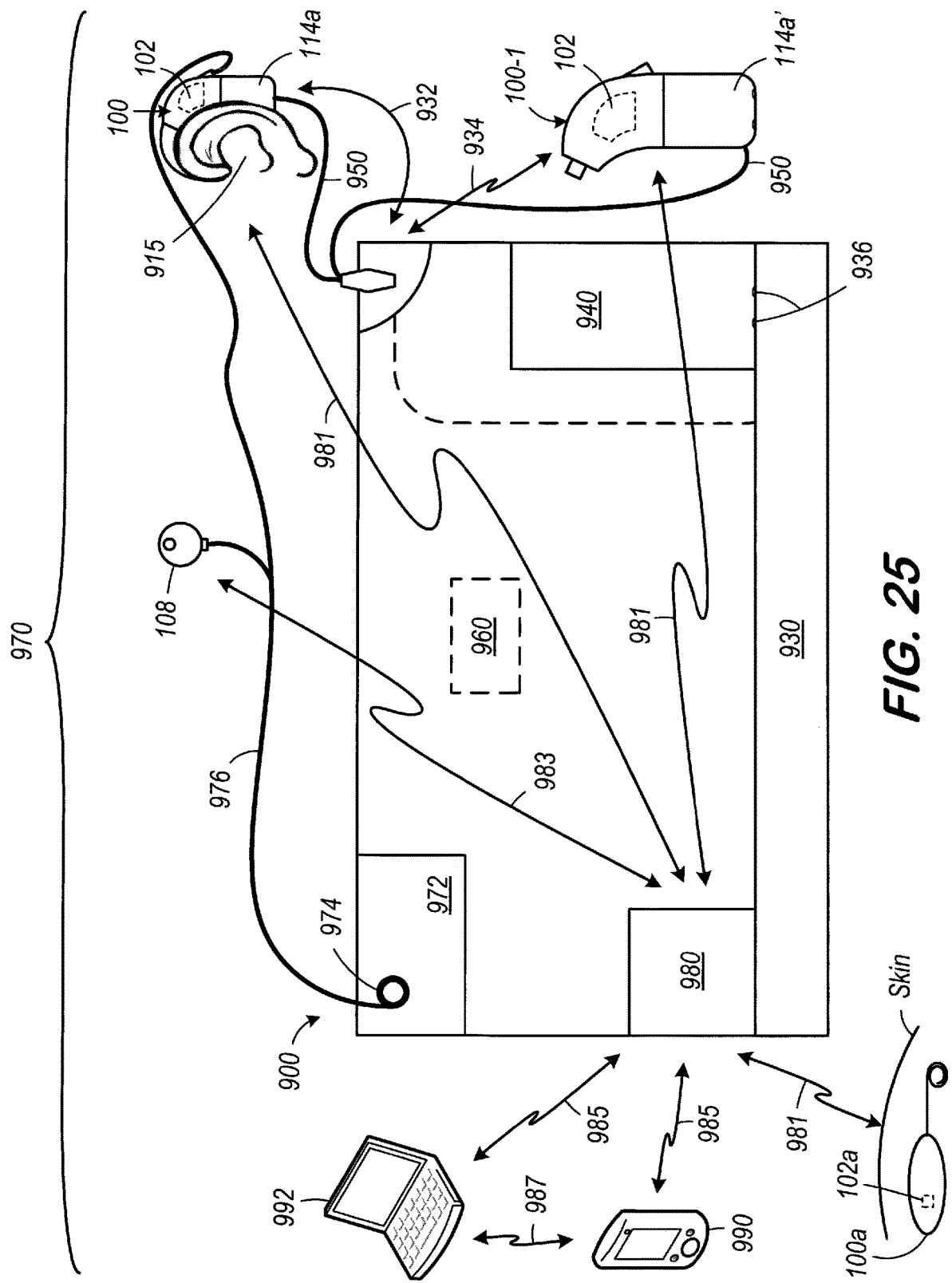
FIG. 25 is a diagram of a cochlear implant system including a speech processor case in accordance with one embodiment of a present invention and other aspects of the system.

FIG. 25 is a diagram of a case 900, in accordance with at least one of the present inventions, that is capable of communicating with a BTE unit 100 on the ear 915, housing and/or communicating with a BTE unit 100-1 off the ear, and communicating with other cochlear implant system devices. The case 900 may include a rechargeable or primary battery 930 or other power source, such as that shown in FIG. 26.

The battery 930 provides power for the operations of the case 900. The battery 930 may also provide power to charge and simultaneously provide power to operate the speech processor unit 100 through inductive current 932 (e.g., 27 MHz) to the BTE unit 100 while on the ear. Additionally or alternatively, the battery 930 may also provide power to charge and simultaneously provide power to operate the BTE unit 100-1 through an inductive current 934 (e.g., 27 MHz) while the BTE 100-1 is off the ear or through direct electrical contacts 936 while the BTE unit 100-1 is docked within a docking station 940 of the case 900. Alternatively, the battery 930 may provide power to either BTE unit 100 or 100-1 through a direct wire or cable 950 connection whether or not the BTE units 100 or 100-1 are docked with the case 900. The cables 950 are connected to the BTE units 100 and 100-1 by way of batteries 114a and 114a' that may be connected (either permanently or temporarily) to the cables.

The case 900 may also include a second speech processor 960 (as distinguished from the first speech processors 102 in the BTE units 100 and 100-1). The second speech processor 960 may provide functionality to the operation of the ICS system 970 used by a patient with impaired hearing. This functionality may replace or augment the functionality already provided by either of the speech processors 102. The processor 960 may augment either of the speech processors by providing additional functions created to work in conjunction with the existing or newly programmed operations of speech processors 102. The processor 960 may also replace the functional operations of either of the speech processors 102 by issuing a control token which effectively permits the processor 960 to override the internal operations of the processors 102. Further, speech processor 960 is available as a backup processor that can provide the functions necessary for a patient to hear when the either of the first speech processors 102 cease normal functioning.

The case 900 may also include communications electronics 980 capable of wirelessly or directly (through wire, cable, or direct electrical contact) communicating with communications electronics contained in the BTE units 100 and/or 100-1. The case 900 may also communicate wirelessly with the communications electronics contained in an implanted speech processor unit 100a. For example, such communications electronics 980 (e.g., an ITEL communications microchip) may permit 10.8 MHz transfer of information 981 to and from either of the speech processor units 100, 100a, and 100-1. The ITEL 10.8 MHz communications link provides the case 900 with the ability to command or program the speech processors 102 and 102a of the units 100, 100-1 and 100a to transfer audio information, and to effectively act as a master device remote control or programming unit of the units 100, 100-1 and 100a as slave devices.

The case 900 may also establish a wireless communication link 983 or direct communications link with a headpiece 108. As explained earlier, the headpiece 108 transmits a stimulation sequence having varying pulse widths and amplitudes to an implanted receiver circuit of the ICS system. The implanted receiver circuit is connected to an implantable electrode array that has been inserted into the cochlea of the inner ear. The electrical stimulation current generated by the ICS is applied to varying electrode combinations to create a perception of sound in a patient with impaired hearing. By establishing a communications link 983 between the case 900 and the headpiece 108, the case 900 may transfer information and power in order to permit the headpiece 108 to operate properly. Where the case 900 includes a speech processor 960, the communications link 983 between the case 900 and the headpiece 108 provides the case 900 with the ability to circumvent any similar link that may exist between the unit 100 or 100-1 and the headpiece 108. Alternatively, where the case 900 does not include a speech processor 960, the communications link 983 may act as an alternate communications link to any similar link that may exist between the units 100 and 100-1 and the headpiece 108.

In addition, communications electronics 980 may provide the case 900 with the ability to establish a communication link 985 with a clinician's programming interface (CPI) unit 990, a clinician's fitting station 992, and/or other external devices. Such communications electronics 980 may facilitate the transfer of information and/or power to and from the case 900 other external devices. The CPI unit 990, alone, alternate to, or in conjunction with clinician's fitting station 992 and/or other external devices (e.g., through another communication link 987) may be used to test and reprogram the operational parameters of the speech processor 960. Further, by communicating with the case 900, which case 900 in turn communicates with potential slave devices such as BTE units 100 and 100-1, the CPI unit 990, clinician's fitting station 992, and/or other external devices have the ability to indirectly test and/or reprogram the operational parameters of such slave devices. Alternately or additionally, the case 900 may be effectively used as a clinician's programming unit to prepare and send at least one program defining a set of stimulation parameters directly to a speech processor unit.

Where the case 900 communicates (information or power) with any external devices including BTE unit 100, BTE unit 100-1, headpiece 108, CPI unit 990, and clinician's fitting station 992 using a wire or cable 976 to connect the case 900 to each respective device, the wire or cable 976 may be a single cable or may be bifurcated (to connect two or more devices to the case 900 at the same time). The cable 976 may be manually wrapped and placed within a cable receptacle 972 within the housing of the case 900. The cable receptacle 972 may include a spring-loaded reel or equivalent structure 974 capable of winding or retracting the cable 976 into the housing of the case 900 when the cable 976 is not in use.

Figure 26:
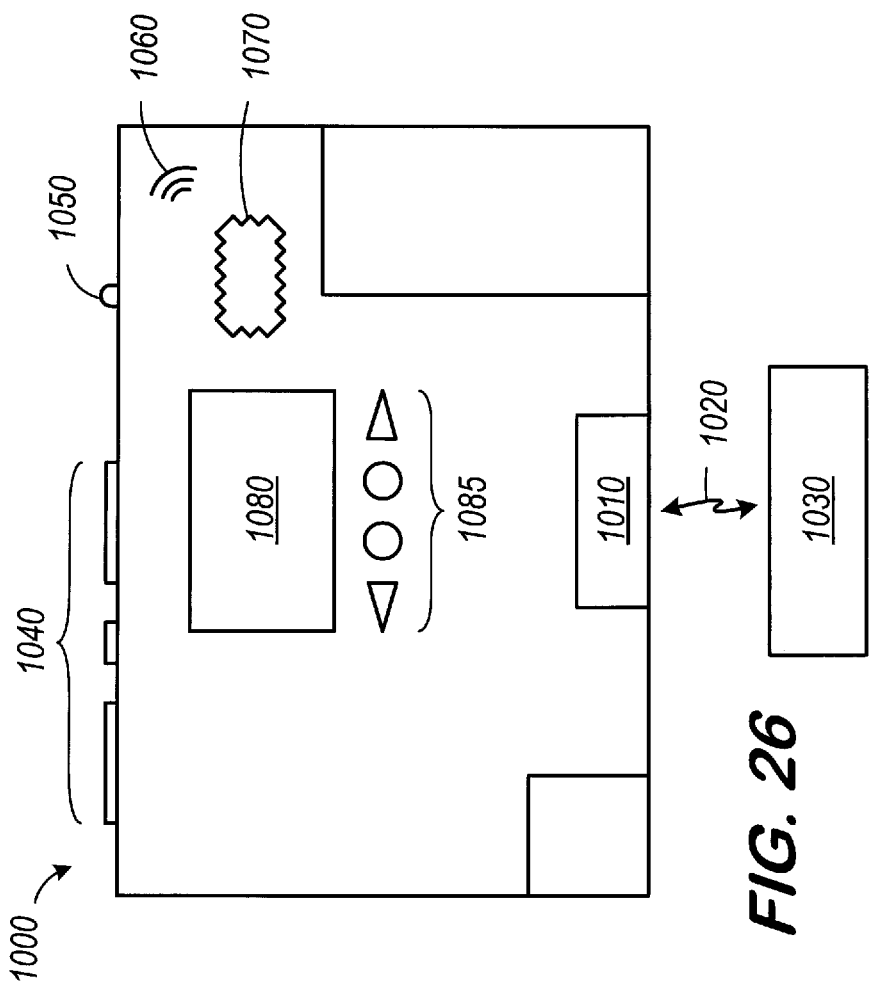
FIG. 26 is a front view of a speech processor case in accordance with one embodiment of a present invention.

The case 900 may include many other features, elements, and benefits as described in FIG. 26 and throughout this specification.

FIG. 26 is a diagram of a case 1000 in accordance with at least one of the present inventions that receives power to an antenna coil 1010 or equivalent structure through an inductive link 1020 from an external source 1030. The case 1000 may also include other power sources such as a rechargeable or primary battery as explained above with reference to FIG. 25. The inductive link 1020 provide operational power for the desired functions of a case of the present invention.

Also exemplified in FIG. 26, a user can control various operations of the case 1000 through control actuators 1040 on any surface of the case 1000. The actuators 1000 may include buttons, wheels, switches, and other various structures capable of modifying various operational parameters of the case 1000 including volume, power, stimulation program selection, sensitivity, and other parameters.

Further, a case in accordance with at least some of the present inventions may include at least one of a variety of status indicators. Status indicators are exemplified in FIG. 26 as an LED light indicator 1050, a speaker or acoustic indicator 1060, and a buzzer or motion indicator 1070. Such indicators may be electronically linked to various electrical and/or mechanical components of the case 1000 in order to indicate the various statuses of the case 1000 during operation. For example, buzzer 1070 may vibrate when the battery (shown in FIG. 25 as battery 930) is almost fully depleted. The LED light 1050 may light red when a BTE unit is not properly docked with the case. And, the speaker 1060 may sound various alarms when the coil 1010 is not properly aligned with the external power source 1030. Any other known operation that is necessary or desired for the functioning of a case of the present invention may "displayed" or communicated to a patient by associating the desired function with signal provided by a status indicator of the present invention. Any number of any indicator or combination thereof may be used to provide any pattern, intensity, frequency, and/or duration of visual, audio, and motion signals to a user.

A liquid crystal display (LCD) 1080 may function as both a status indicator and a control for the case 1000. LCD 1080 may display both text and graphics necessary or desired for use during the various operations of a case of the present invention. LCD 1080 may be accompanied by actuators or controls 1085 that permit a user to input information into the case 1000 and thus view and control its operations. Additionally or alternatively, actuators or controls 1085 or any other actuators or input device (e.g., a keyboard) may be used to prepare and send a program defining at least one set of stimulation parameters from the case 1000 to any speech processor.

Case 900 of FIG. 25 and case 1000 of FIG. 26 may provide access to controls on a docked first BTE unit and/or include actuators on the case 900 and/or 1000 that correspond with controls of the first BTE unit. Such access and/or controls are described in more detail with reference to FIGS. 27 and 28.

Figure 27:
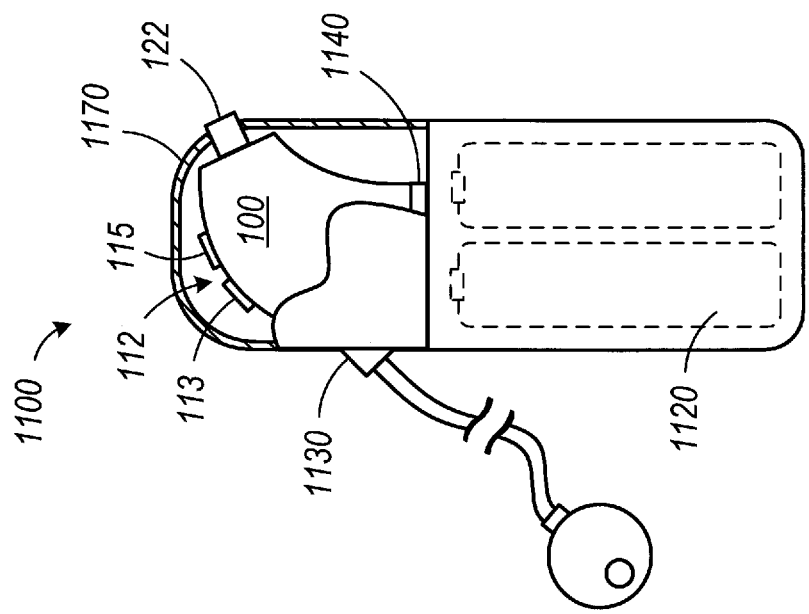
FIG. 27 is a front, partial section view of a speech processor and a speech processor case in accordance with one embodiment of a present invention.

FIG. 27 is a side view of a BTE unit 100 detached from a BTE battery pack and docked within a case 1100 in accordance with at least one of the present inventions. The BTE unit 100 easily fits into the case 1100 and established a mechanical connection with the case 1100 and an electrical connection with the components of the case 1100 by way of a slide-in BTE interface 1140. The BTE unit 100 receives operational power from a power source such as two AA batteries 1120 loaded into the case 1100. Alternately, an inductive or rechargeable power source could be used with case 1100. Case 1100 connects the headpiece cable port 106 (FIG. 1) of the BTE unit 100 to a radio frequency (RF) port 1130 on the case 1100. A transmitter or other communications technology of the RF port 1130 is capable of communicating with a headpiece via RF communications rather than through a cable or wired connection. Alternatively, the case 1100 may provide physical access to the headpiece cable port 106 (FIG. 1) of the BTE unit 100 so that a user may manually connect a cable to the a headpiece and the BTE unit 100.

The case 1100 also permits a user to access to the control panel 112, which may include a program selector switch 113 and a volume control wheel 115. The case 1100 also permits access to the auxiliary device connector connector 122 (or "port") of the BTE unit 100. The case 1100 may also include at least one control cover 1170 which may be opened when a patient desires to access any of the switch 113, wheel 115, port 122, and/or other controls and features. The at least one control cover 1170 may be closed to protect and prevent unwanted access to such controls and features. Alternatively or additionally, the at least one control cover 1170 may protect the unit 100 from wind, moisture, and other elements. Alternately or additionally, the case 1100 may include actuators that provide indirect access and control over such controls and features as further described below with reference to FIG. 28.

Figure 28:
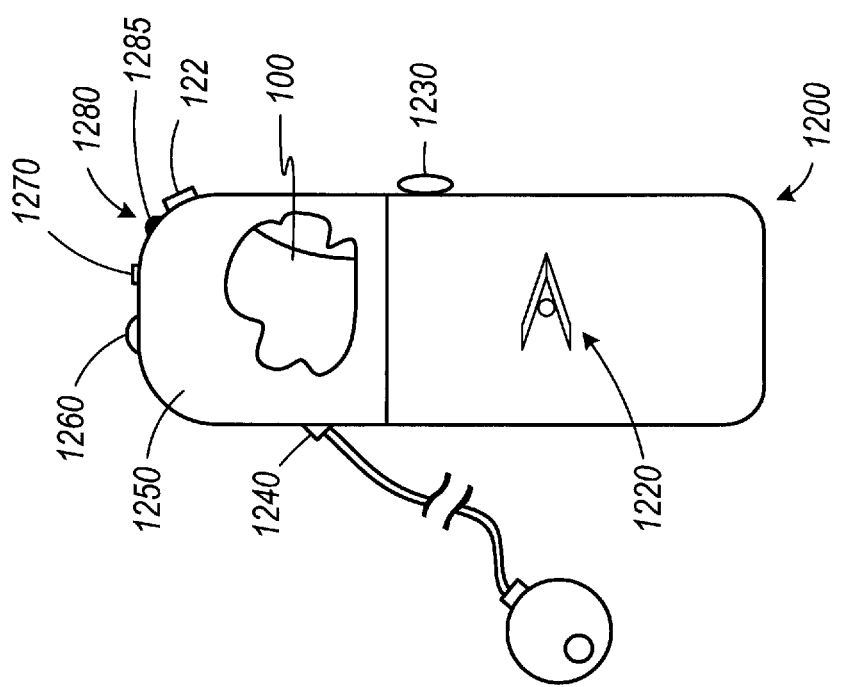
FIG. 28 is a front, cutaway view of a speech processor and a speech processor case in accordance with one embodiment of a present invention.

FIG. 28 is a side view of a BTE unit 100 docked within a case 1200 in accordance with at least one of the present inventions. The case 1200 may include a clip or safety pin 1220, a lanyard ring 1230, a belt loop, or other similar means of attaching the case 1200 to the clothing or body of a patient.

Case 1200 may include additional structure and materials 1240 capable of protecting the BTE unit 100 and its components from water, wind, or other detrimental physical contact. Such structure and materials 1240 may provide a water proof or at least water resistant environment for the proper operation of the BTE unit 100. Such structure and materials 1240 may also permit a user to participate in sports involving physical contact and other activity likely to jolt the BTE unit 100 without damaging the BTE unit 100. Structure and materials, such as extra padding, hard polymers, and soft polymers will be understood and appropriately applied by those of ordinary skill in the art to the present invention.

Case 1200 may also include actuators 1250 that permit a user to actuate controls or features of the BTE unit 100 or similar speech processor unit while such controls or features from the outside environment. For example, a volume control wheel on the BTE unit 100 would correspond with a wheel actuator 1260 on the case 1200. The wheel actuator 1260 would, when turned by the patient, turn the underlying wheel on the BTE unit 100. Similarly, a button actuator 1270 on the case 1200 would correspond and actuate with an underlying button on the surface of the BTE unit 100. Alternatively or additionally, the button actuator 1270 or other actuator of the case 1200 may be linked to electronics within the case 1200 which are electrically connected to the electronics of the BTE unit 100. Thus, when a patient pressed the button actuator 1270, the underlying button on the BTE unit 100 would be pressed and/or an electrical signal would travel from the case 1200 to the BTE unit 100, and a corresponding control response on the BTE unit 100 would be initiated. Such actuators may be an enlarged version of their respective BTE unit 100 counterparts, thus providing easy access and control for users with challenged dexterity. The actuators 1250 may include buttons, wheels, switches, and other various structures capable of modifying various operational parameters of the case 1200 including volume, power, stimulation program selection, sensitivity, and other parameters.

Case 1200 may also include a microphone 1280 that provides a source of audio input independent of the auxiliary input 122 of the BTE unit 100 or any other cable or wireless microphone input described above. The open microphone 1280 may be protected from the elements, i.e., wind and water, by a cover 1285 that may be wind and water resistant, yet provide sound to permeate the cover 1285 without substantially changing the shape of the sound waves. Such cover 1285 may include micro-holes or may be a mesh or net for example.

Figure 29:
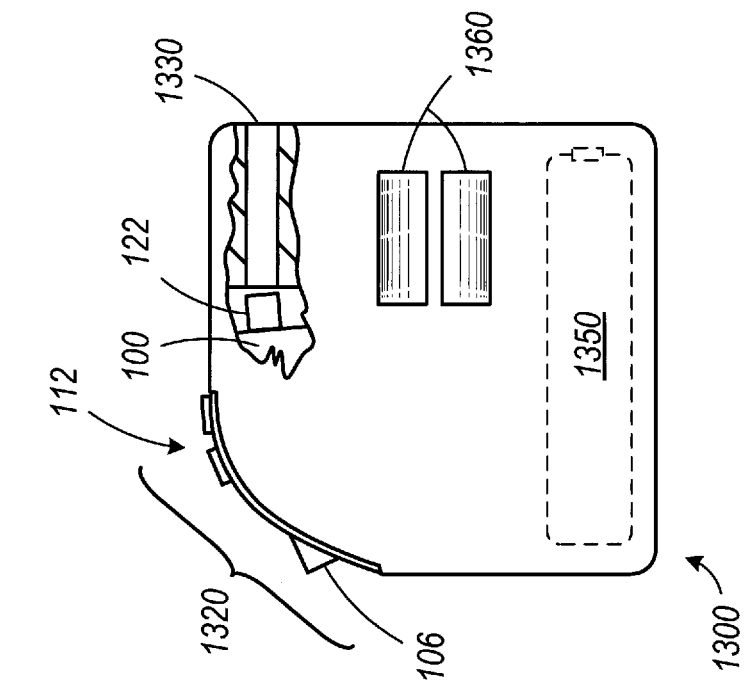
FIG. 29 is a rear, cutaway view of a speech processor and a speech processor case in accordance with one embodiment of a present invention.

FIG. 29 is a side view of a BTE speech processor unit 1310 docked within a substantially square case 1300 in accordance with at least one of the present inventions. Case 1300 provides access 1320 to various controls and features (e.g., the control panel 112 and headpiece port 106) and access 1330 to the auxiliary input port 122 of the BTE unit 100. Case 1300 also includes a power source 1350 and a belt loop or clip 1360 that permits the case 1300 to be secured to a patient's body with a belt, strap, or similar structure. Case 1300 is essentially a simplified embodiment of the present invention which permits the use of the existing controls on the BTE unit 100 with other limited (rather than full or extensive) built-in features described throughout this disclosure.

Figure 30:
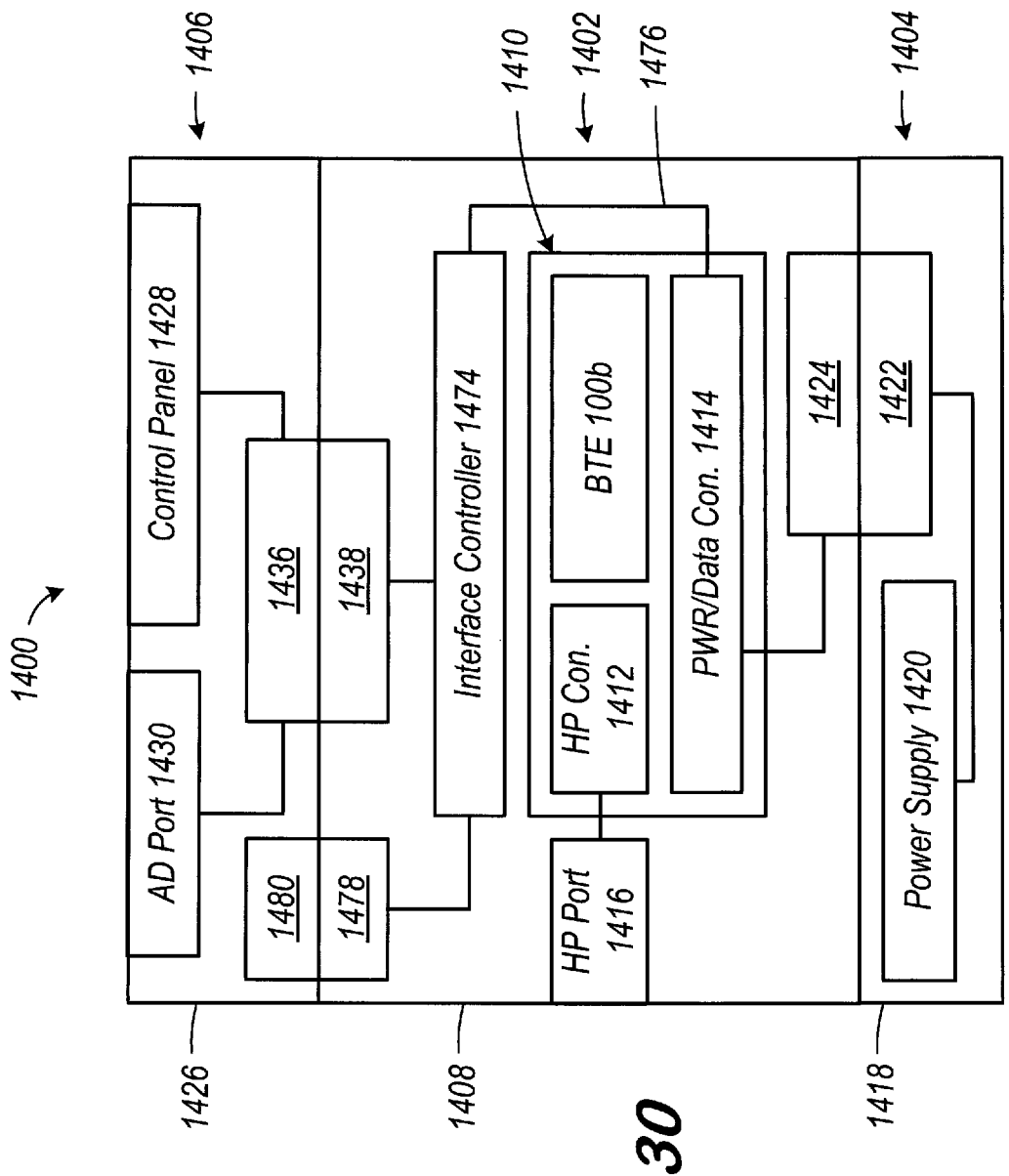
FIG. 30 is a functional block diagram of a speech processor and a speech processor case in accordance with one embodiment of a present invention.

Turning to FIG. 30, another speech processor case in accordance with at least some of the present inventions, which is generally represented by reference numeral 1400, includes a main portion 1402 in which a BTE unit 100b is stored, a power portion 1404 and a control portion 1406. The BTE unit 100b may be essentially identical to the BTE unit 100 described above, but for the headpiece port arrangement described below with reference to FIGS. 40-41, and similar elements are identified by similar reference numerals. The main portion 1402, power portion 1404 and control portion 1406 in the illustrated implementation are separate structural elements that may be physically and electrically connected (or "docked"), disconnected from one another, and re-connected. In other implementations, any two or all three of the these elements may form part of a single, integral unit as, is also discussed below.

As illustrated for example in FIGS. 30-33, the main portion 1402 includes a housing 1408 with an internal BTE storage region 1410. A headpiece connector 1412 (e.g., an RF connector) and a power/data connector 1414, which are located within the BTE storage region 1410, electrically connect the BTE headpiece connector 106b and the BTE power/data connector 116b to the speech processor case 1400 in the manner described below with reference to FIGS. 40-46. The headpiece connector 1412 is, in turn, connected to a headpiece port 1416 (e.g., an RF port) on the exterior of the housing 1408. As a result, a headpiece (e.g., headpiece 108 in FIG. 1) may be connected to a BTE unit (e.g., BTE unit 100a) by way of the case 1400 and, more specifically, by way of the headpiece connector 1412 and port 1416.

The exemplary power portion 1404, which includes a housing 1418 and a power supply 1420, may be used to provide power for the main portion 1402, a BTE unit within the main portion, and the control portion 1406. A wide variety of power supplies may be employed. For example, the power supply 1420 may be one or more replaceable and/or rechargeable batteries. In other implementations, the power portion may be configured to receive and electrically connect to the removable BTE power supply (e.g., power supply 114b in FIG. 41). An electrical connector 1422 (e.g., a pair of contacts) is provided on the exterior of the power portion housing 1418 and a corresponding connector 1424 is provided on the main portion housing 1408.

Figure 31:
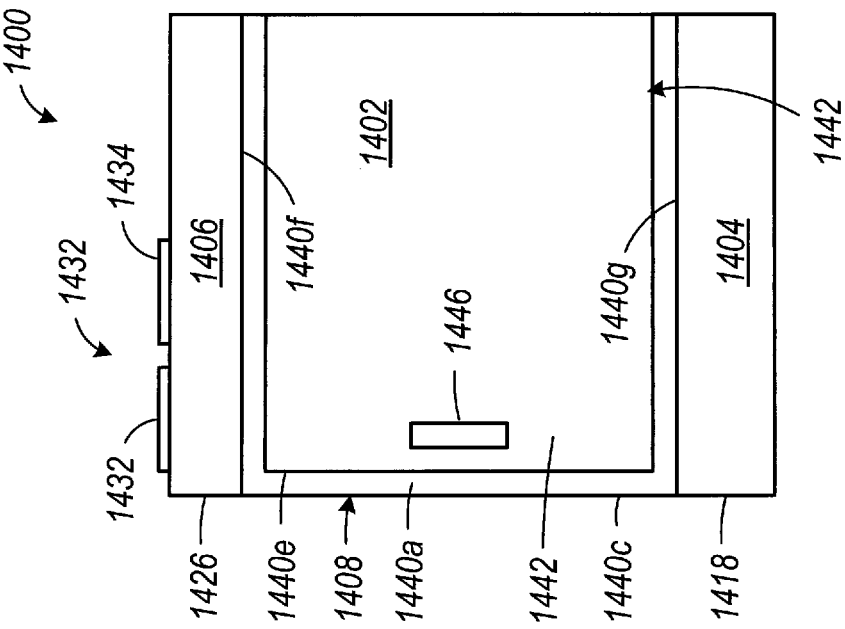
FIG. 31 is a front view of an exemplary implementation of the speech processor case illustrated in FIG. 30.
Figure 38:
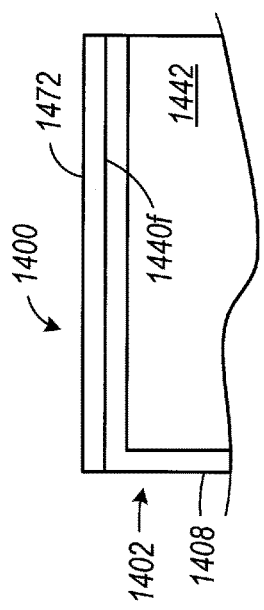
FIG. 38 is a partial side view of the speech processor case illustrated in FIG. 31 with the control portion removed and replaced by a cover.

The control portion 1406 may be used to control various aspects of the main portion 1402 and/or a BTE unit within the main portion. In the illustrated embodiment, the control portion 1406 includes a housing 1426, a control panel 1428, and an auxiliary device port 1430. The control panel 1428 may, as illustrated in FIG. 31, include a volume knob 1432 and a program selector switch 1434. An electrical connector 1436 (e.g., a plurality of electrical contacts) is provided on the exterior of the control portion housing 1426 and a corresponding connector 1438 is provide on the main portion housing 1408.

The exemplary speech processor case 1400 may also be provided with a wireless transceiver (not shown) such as, for example, an FM transceiver that allows wirelessly transmitted signals to be received by, and transmitted from, the BTE unit 100a, as is described above in the context of other embodiments. A wireless transceiver may be located in one or more of the main portion 1402, power portion 1404 and control portion 1406.

The exemplary speech processor case 1400 may also be provided with one or more audible, visible and/or otherwise perceptible indicator devices (not shown), such as a speaker or buzzer, an LED or other light source and/or a vibrator. The indicator device(s) may be used to provide and audible, visible and/or otherwise perceptible indication as to the status of components of the BTE unit 100a and/or the case 1400, as is described above in the context of other embodiments. Such indicators may be located in one or more of the main portion 1402, power portion 1404 and control portion 1406.

A belt loop or clip (not shown), or other suitable mounting device (e.g. a lanyard ring or safety pin), may be secured to the exterior of the main portion 1402 and used to secure the case to the clothing or body of the user.

Figure 33:
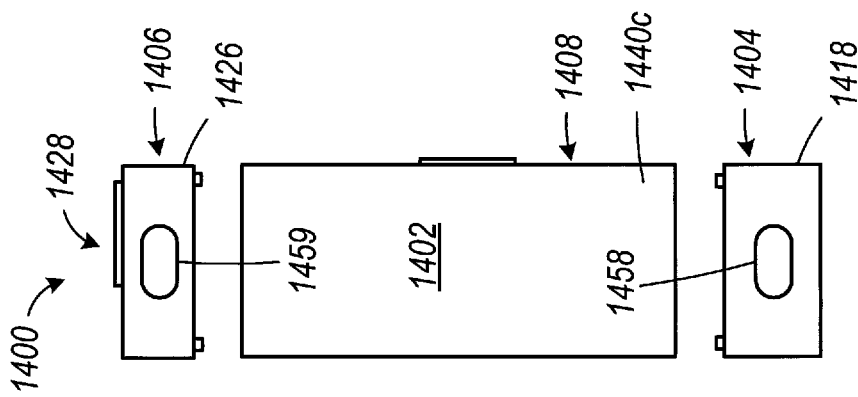
FIG. 33 is an exploded side view of the speech processor case illustrated in FIG. 31.
Figure 32:
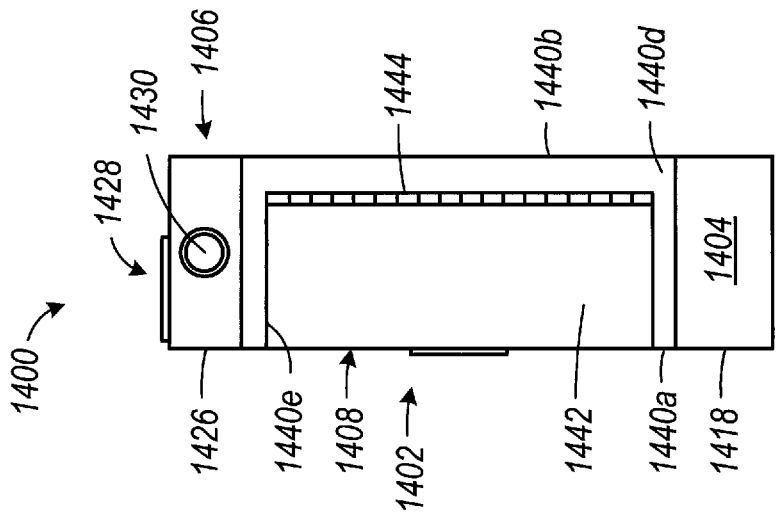
FIG. 32 is a side view of the speech processor case illustrated in FIG. 31.

Referring more specifically to FIGS. 31-33, the exemplary main portion housing 1408 includes a front wall 1440a, a rear wall 1440b, side walls 1440c and 1440d, an opening 1440e in the front wall 1440a and side wall 1440d, a top wall 1440f, and a bottom wall 1440g. A cover 1442, which permits access to the BTE storage region 1410 (FIGS. 30 and 39) when open and maintains a moisture-proof seal when closed, may also be provided. The exemplary cover 1442 has an overall L-shape, is pivotable about a hinge 1444 on the side wall 1440d, and may include a handle 1446. A latching mechanism (not shown) may also be provided to maintain the cover 1442 in the closed position until the user intends to open the case.

Turning to the manner in which the power portion 1404 is mechanically and electrically connected to the main portion 1402 in the exemplary implementation, and referring to FIGS. 34 and 35, the power portion housing 1418 includes a top wall 1448 with a plurality of mechanical connectors 1450 (e.g., portions of latch mechanisms). Corresponding connectors 1452 are provided on the bottom wall 1440g of the main portion housing 1408. The electrical connector 1422 on the power portion 1404 consists of a pair of electrical contacts 1454 on the top wall 1448, while the electrical connector 1424 on the main portion 1402 consists of a corresponding pair of electrical contacts 1456 on the bottom wall 1440g. A release button 1458 (FIG. 33), which facilitates disconnecting of the power portion 1404 from the main portion 1402 (e.g., latch release), may be provided on the power portion or the main portion. The power portion 1404 may be detached to, for example, recharge or replace the power supply 1420.

As illustrated in FIGS. 36 and 37, the control portion housing 1426 in the exemplary embodiment includes a bottom wall 1458 with a plurality of mechanical connectors 1460 (e.g., portions of latch mechanisms). Corresponding connectors 1462 are provided on the top wall 1440f of the main portion housing 1426. The electrical connector 1436 on the control portion 1406 consists of a plurality of electrical contacts 1464, while the electrical connector 1424 on the main portion 1402 consists of a corresponding plurality of electrical contacts 1466. The electrical contacts 1464 and 1466 may be in the form of pins, pads or any other suitable device. An alignment locator feature, such as a post 1468 and an opening 1470 that receives the post and keys orientation, is also provided.

The control portion 1406 may be a removable aspect of the case 1400 because it includes various elements that are only required from time to time (e.g., the volume knob 1432) or are merely useful options (e.g., the auxiliary device port 1430). A release button 1459 (FIG. 33), which facilitates disconnecting of the control portion 1404 from the main portion 1402 (e.g., latch release), may be provided on the control portion or the main portion. Additionally, and referring to FIG. 38, the case 1400 may also include a cover 1472, with the same mechanical connectors (not shown) as the control portion housing 1426, that may be used to protect the electrical connector 1438 when the control portion 1406 is not in use. Other instrumentalities for protecting the electrical connector 1438 are described below.

In the illustrated embodiment, the case main portion 1402 supplies power to the control portion 1406 by way of at least some of the contacts 1464 and 1466 on the electrical connectors 1424 and 1436 (FIGS. 36-37). To that end, and referring again to FIG. 30, the case main portion 1402 also includes an interface controller 1474 that selectively supplies power (e.g., DC power) to one or more of the contacts 1466. In particular, the interface controller 1474 may be configured to supply power to one or more of the contacts 1466 in response to the control portion 1406 being docked to the main portion 1402, and to not supply power to the contacts 1466 when there is not a control portion docked to the main portion. One such contact is contact 1466a, which is the power supply contact that powers the control portion 1406. Other contacts 1466a may also be selectively connected to, and disconnected from, a voltage bias or other power source in response to docking. The power/data connector 1414 in the BTE storage region 1410 may be connected to the appropriate contacts 1466 by way of the interface controller 1474 and a flex cable 1476.

The exemplary case main portion 1402 may be provided with a sensor that senses when the control portion 1406 is docked to the main portion. The sensor supplies a signal to the interface controller 1474 (FIG. 30) which indicative of the presence (or absence) of the control portion 1406 and the interface controller supplies power to the appropriate electrical contacts 1466 in response to the signal being indicative of the presence of the control portion 1406. There are a number of advantages associated with only supplying power to the electrical contacts 1466 when the control portion 1406 is docked to the main portion 1402. For example, supplying power to the contacts 1466 increases the likelihood that they will corrode in the presence of salts, water and some chemicals such as (collectively "corrosive substances") because the power supplies electromotive force that drives corrosion. In view of the fact that (1) there is no reason to supply power to the electrical contacts 1466 when the main portion 1402 is not connected to the control portion 1406 and (2) the electrical contacts 1466 are more likely to be exposed to corrosive substances when the control portion has been removed (e.g., for exercise), selectively supplying power to the contacts in the manner described above reduces the likelihood of corrosion without degrading the functionality of the case 1400.

A wide variety of sensors may be employed. Referring to FIGS. 30, 36 and 37, in the illustrated implementation, the main portion 1402 includes a magnetic sensor 1478, such as a switch that changes state (i.e., opens or closes) when a magnet is in close proximity thereto or a device that provides digital or analog output based on the proximity of a magnet thereto, and the control portion 1406 includes a magnet 1480. The magnetic sensor 1478 and magnet 1480 may be positioned such that the magnetic field of the magnet at the magnetic sensor will only be strong enough to change the state of the sensor (or otherwise be sensed) when the control portion 1406 is secured to the main portion 1402 by way of the mechanical connectors 1460 and 1462. Additionally, the magnetic sensor 1478 and magnet 1480 may be located inwardly of the outer surface of the housings 1408 and 1426, as shown, or the magnetic sensor and/or magnet may be carried on the outer surface of the associated housing. Suitable magnetic sensors include, but are not limited to, magnetoresistive sensors, Hall effect sensors, and reed switches. By way of example, but not limitation, suitable magnetoresistive switches include those in the AS series of anisotropic-magneto-resistance (AMR) sensors from Murata Manufacturing Co., Ltd. (e.g., the AS-M15SA-R). Other suitable magnetic sensors include giant magnetoresistive (GMR) sensors from NVE Corporation. In other implementations, mechanical switches may be employed in place of the magnet and sensor. Additional details concerning the above-described interface controller and sensor arrangement may be found in U.S. Pat. Pub. No. 2011/0103627, which is incorporated herein by reference.

Figure 39:
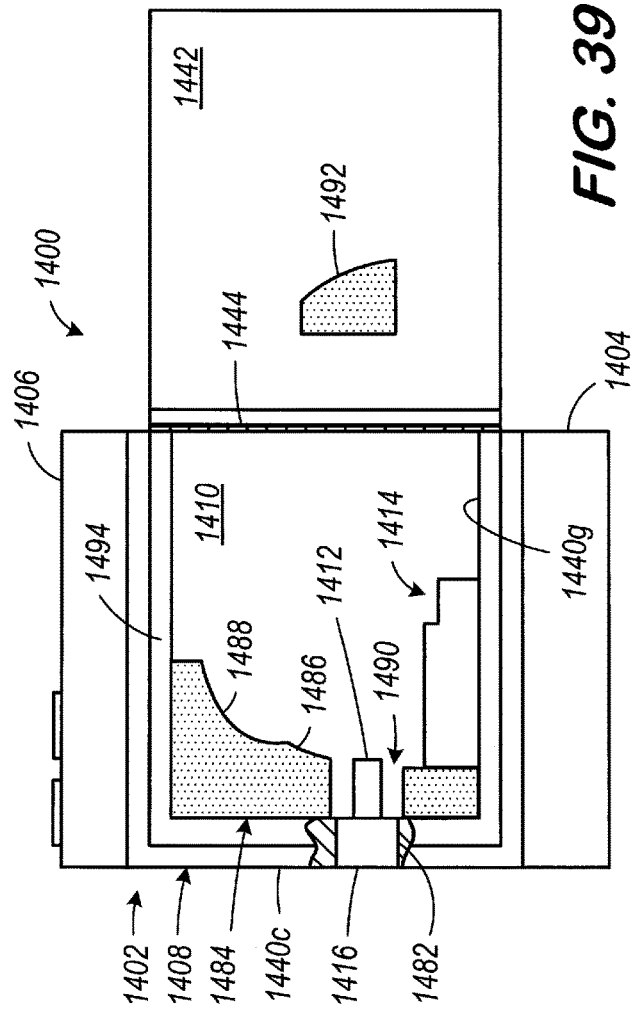
FIG. 39 is a front view of the speech processor case illustrated in FIG. 31 in an open state.

Turning to FIG. 39, and as noted above, the BTE storage region 1410 of the exemplary case 1400 includes the headpiece connector 1412 and power/data connector 1414. The headpiece connector 1412 and power/data connector 1414 are configured such that they will both mate with the corresponding connectors on the BTE unit, e.g., the headpiece port 106b and the power/data connector 116b on the BTE unit 100a (discussed below), when the BTE unit is docked within the case 1400. The headpiece connector 1412 and headpiece port 1416 are each part of a unitary structure (discussed below with reference to FIG. 40) that is mounted within an aperture 1482 in the housing side wall 1440c. The power/data connector 1414 is a slide-in connector that is mounted on the bottom wall 1440g. The BTE storage region 1410 also includes an abutment 1484, such as a plastic insert, that contacts the BTE unit as the BTE unit completes the docking process. The abutment 1484 includes a surface 1486 with a curved shape that corresponds to the shape of the BTE unit, an indentation 1488 for the BTE unit control panel, and an opening 1490 that allows the BTE unit headpiece connector to engage the case headpiece connector 1414.

In the illustrated implementation, friction between the BTE unit connector and the case connectors maintain the BTE in the docked position. A second abutment 1492 may be provided on the cover 1442. The second abutment 1492 engages the opposite side of the BTE unit when the cover 1442 is closed to prevent movement of the BTE unit from the docket position due to, for example, vibration. Alternatively or in addition, a latch mechanism (not shown) may be provided to maintain the docked position of the BTU unit.

As can also be seen in FIG. 39, the housing front wall 1440a may include an indentation 1494 so that the cover 1442 will be flush with the front wall when the cover is closed (FIGS. 31-32). The indentation 1494 may include seals (not shown) to prevent moisture ingress.

As illustrated in FIG. 40, an although the present inventions are not limited to such a connector, the exemplary headpiece connector 1412 and headpiece port 1416 may be combined into a unitary (and typically waterproof) connector 1495 that includes a female plug 1496 and a male plug 1498 which allows the connector to serve as an intermediary between male and female connectors (e.g., a headpiece connector and a BTE headpiece port) that would otherwise be connected to one another. The female plug 1496 performs the function of the headpiece port 1416, and the male plug 1498 performs the function of the headpiece connector 1412. The female plug 1496 is configured to receive the male plug 217 on a headpiece cable 219 (FIG. 46) in the essentially same manner as a BTE headpiece port (e.g., BTE headpiece port 106*a*) and the male plug 1498 is configured to be received by a BTE headpiece port in essentially the same manner as the male plug one a headpiece cable. The female plug 1496 and male plug 1498 may share certain structural elements, as is discussed below in the context of the exemplary embodiment, or may be entirely separate structures that are electrically connected to one other. Additionally, although the exemplary structures are generally cylindrical in overall shape, other shapes (e.g., rectangular) may be employed.

With respect to the structures that are common to the female plug 1496 and male plug 1498, the exemplary unitary connector 1495 includes a common conductor 1500 and a common insulator 1502. The common insulator includes a lumen 1503 through which the common conductor passes. The common conductor 1500 may be formed from suitable electrically conductive materials such as, for example, beryllium copper or brass. Suitable electrically insulating materials for the common insulator 1502 include, but are not limited to, polytetrafluoroethylene (PTFE) and polyoxymethylene (POM).

The exemplary female plug 1496 includes a socket 1504, which is part of the common conductor 1500, a barrel 1506, and an insulator 1508, which is part of the common insulator 1502, located between the socket and the barrel. The barrel 1506 has a main portion 1510, with an inner surface 1512 that defines an open region 1514, an integral flange 1516, and a recess 1518. The barrel 1506 may be formed from suitable electrically conductive materials such as, for example, beryllium copper or brass. The insulator 1508 has a main portion 1520 that covers the socket 1504 and a flange 1522 that is located in the barrel recess 1518.

The exemplary male plug 1498 includes a center conductor 1524, which is part of the common conductor 1500, an outer conductor 1526, and an insulator 1528, which is part of the common insulator 1502, located between the center conductor and the outer conductor. The outer conductor 1526 has an annular barrel 1530 with gaps 1532 and protrusions 1534, and a flange 1536. The gaps 1532 allow the barrel 1530 to flex inwardly when the plug 1498 is inserted into the corresponding connector, and the protrusions engage the inner surface of the corresponding connector. The flange 1536 abuts, and is electrically connected to, the flange 1516 of the female plug barrel 1506. Suitable materials for the outer conductor 1526 include, but are not limited to, beryllium copper and brass. The exemplary insulator 1528 has a relatively large diameter portion 1538 with an outer surface that abuts the inner surface of the outer conductor barrel 1530 and a relatively small diameter portion 1540 that is separated from the inner surface of the outer conductor barrel by a small gap 1542. An open region 1544 is formed in the relatively small diameter portion 1540. The gap 1542 allows barrel 1530 of the outer conductor 1526 to flex inwardly, and the open region 1544 accommodates the socket of the corresponding connector.

With respect to waterproofing, the exemplary unitary connector 1495 is provided with a seal 1546 that is compressed between the barrel flange 1516, the insulator flange 1522 and the outer conductor flange 1536, as well as a seal 1548 that is compressed between the common conductor 1500 and the common insulator 1502. The seals 1546 and 1548 prevent moisture from passing through the connector, and may be carried in indentations 1550 and 1552. With respect to preventing moisture from passing between the main portion housing 1408 and the unitary connector 1495, a seal 1554 is compressed within the aperture 1482 between the housing wall 1440*c* and the female plug barrel 1506. Suitable materials for the internal seals 1546, 1548, and 1554 include, but are not limited to, elastomeric materials such as silicone rubber, Neoprene synthetic rubber, urethane, and soft polyvinyl chloride (PVC). In at least some implementations, the seals will have a sealing effectiveness of at least IEC IPX7.

As alluded to above, the exemplary BTE unit 100*b* may be docked within the case 1400 when the power supply 114*b* is removed. This aspect of the operation is discussed below with reference to FIGS. 44-46. Referring first to FIG. 41, the exemplary headpiece port 106*b* on the BTE unit 100*b* and the exemplary headpiece connector 1412 (e.g., the male plug 1498 in FIG. 40) within the case 1400 both extend horizontally, i.e. parallel to the direction of sliding movement during the docking process. The interior of the headpiece port 106*b* is configured in a manner substantially similar to the female plug 1496 (FIG. 40) and, accordingly, will mate with the headpiece connector 1412 (e.g., the male plug 1498) or a similarly configured plug on the end of a headpiece cable. The exemplary power/data connector 116*b* is associated with the bottom surface of the BTE unit 100*a* and includes a U-shaped recess 1556 and a rectangular projection 1558. As illustrated in FIG. 42, the projection 1558 has a rectangular contact support 1560, with a plurality of electrical contacts 1562, and an abutment 1564. At least two of the electrical contacts 1562 are power contacts and the remainder are data contacts. The exemplary power/data connector 1414 has a corresponding configuration. Turning to FIG. 43, the exemplary power/data connector 1414 includes a top surface 1566, with a rectangular contact support region 1568 and a plurality of electrical contacts 1570 in the support region, and a U-shaped projection 1572. The U-shaped projection 1572 defines a rectangular recess 1574 that is sized and shape to receive the projection 1558. The electrical contacts 1562 will be aligned with the electrical contacts 1570, such that there will be electrical connections, when the projection 1558 is located within the recess and the 1574 and the abutment 1564 engages the free ends of the U-shaped projection 1572. The electrical contacts 1562 and 1570 may be in the form of pins, pads or any other suitable device.

The docking of the BTE unit 100*b* within the case 1400 is illustrated in FIGS. 44-46. While the cover 1442 is open, the BTE unit 100*b* is placed within the storage region 1410 such that the BTE headpiece port 106*b* and the BTE power/data connector 116*b* are aligned with the case headpiece connector 1412 and the case power/data connector 1414 (FIG. 44). The BTE unit 100*a* may then be moved in the horizontal direction, which is identified by the arrow H, unit the BTE headpiece port 106*b* mates with case headpiece connector 1412 and the BTE power/data connector 116*b* mates with the case power/data connector 1414 (FIG. 45). The BTE unit 100*b* is docked within and to the case 1400. The BTE unit 100*b* is also positioned against the abutment 1484. The cover 1442 may then be closed which, in addition to sealing the storage region 1410, brings the second abutment 1492 into contact with the BTE unit 100*b* (FIG. 46).

After the connections are made, the BTE unit 100*a* and case 1400 will together define a body worn speech processor unit that may, for example, be mounted on an infant harness or the clothing of an adult. A headpiece 216 may then be connected to the case 1400 and, therefore, the BTE unit 100*b*, by the plug 217 on the headpiece cable so that the body worn unit can be used in conventional fashion. The BTE unit 100*b* will be powered by the power supply 1420 (FIG. 30) in the power portion 1404, and may also be controlled by way of the control panel 1428 on the control portion 1406.

The exemplary case 1400 may be modified in a variety of ways. By way of example, but not limitation, the power portion 1404 and the control portion 1406 may be combined into a single, integral unit. The main portion 1402 and the power portion 1404 may be combined into a single, integral unit. The main portion 1402 and the control portion 1406 may be combined into a single, integral unit. The main portion 1402, the power portion 1404 and the control portion 1406 may be combined into a single, integral unit. It should also be noted here that, whether integral or separable, the housings of the main, power and control portions together defined the overall case housing With respect to the BTE unit 100*b*, the BTE unit may be configured such that some or all of the controls on the control panel 112 are disabled when the BTE unit is docked in the case 1400. The BTE unit may also be configured such that it lacks an external control panel such as control panel 112. Here, the BTE unit settings may be set by way of the control panel 1428 or a separate programmer.

Figure 47:
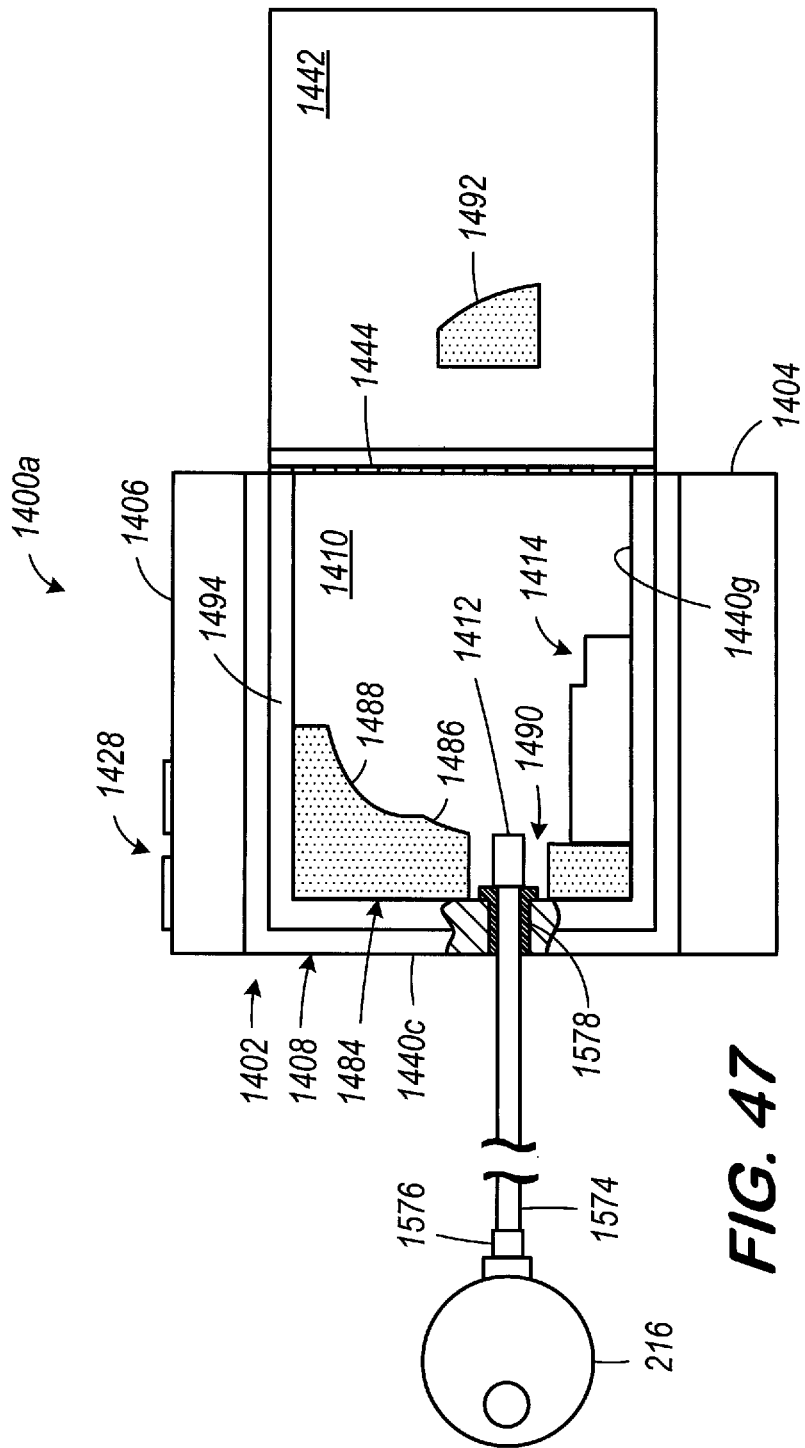
FIG. 47 is a front view of a speech processor case in accordance with one embodiment of a present invention.

In other implementations, the headpiece cable may be an integral (i.e. permanent and not removable in the course of normal use) part of the case. Referring to FIG. 47, the exemplary case 1400*a* is essentially identical to case 1400 and similar elements are represented by similar reference numerals. Here, however, the headpiece port 1416 has been omitted and replaced by a headpiece cable 1574 that extends through the main portion housing 1408. One end of the headpiece cable 1574 is connected to the headpiece connector 1412 (directly as shown or indirectly) and the other end includes a connector 1576 that may be connected to a headpiece (e.g., headpiece 216). An adhesive 1578, such as epoxy, may be used to hold the headpiece cable 1574 in place and create a waterproof seal.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below. The inventions also include speech processor systems consisting of a speech processor unit, such as for example a BTE unit, and any of the speech processor cases described above and/or claimed below.

We claim:

1. A method, comprising the steps of:
   removing an earhook from a behind-the-ear sound processor (BTE) unit that includes an external housing having an exterior, at least one user-manipulatable control element on the exterior of the external housing, a sound processor within the external housing that converts electrical signals from a microphone into a pulse sequence for a cochlear implant, a removable power supply mounted to the external housing, and the earhook;
   placing the entire BTE unit but for the earhook into a BTE storage device that is not part of the BTE unit, that includes water-tight seals, and that is configured to receive the entire BTE unit but for the earhook; and
   connecting a headpiece that is configured to communicate with the cochlear implant to the BTE unit.

2. A method as claimed in claim 1, wherein
   the BTE unit includes a headpiece port; and
   the step of connecting a headpiece to the BTE unit comprises connecting a headpiece that is configured to communicate with the cochlear implant to the BTE unit headpiece port.

3. A method as claimed in claim 2, wherein
   the BTE storage device includes an opening;
   one of the water-tight seals is associated with the opening; and
   the step of connecting a headpiece to the BTE unit comprises connecting a headpiece that is configured to communicate with the cochlear implant to the BTE unit headpiece port by way of the water-tight seal associated with the opening.

4. A method as claimed in claim 3, wherein
   the BTE storage device includes a cover with an open position and a closed position;
   the headpiece is connected to the BTE unit by a cable; and
   the water-tight seal associated with the opening engages the headpiece cable when the cover is in the closed position.

5. A method as claimed in claim 1, wherein
   the step of connecting a headpiece to the BTE unit comprises connecting a headpiece that is configured to communicate with the cochlear implant and is located outside the BTE storage device to the BTE unit headpiece port.

6. A method as claimed in claim 1, wherein
   the microphone is carried on the BTE unit.

7. A method as claimed in claim 1, wherein
   the microphone is carried on the headpiece.

8. A method as claimed in claim 1, wherein
   the BTE storage device includes a cover with an open position and a closed position; and
   the step of connecting a headpiece to the BTE unit comprises connecting a headpiece that is configured to communicate with the cochlear implant to the BTE unit when the cover is in the open position.

9. A method as claimed in claim 1, wherein
   the BTE storage device includes main portion with a storage area that corresponds to the shape of the exterior of the BTE unit and a cover with an open position and a closed position; and
   one end of the cover is secured to the main portion.

10. A method as claimed in claim 1, wherein
    the exterior of the BTE unit external housing defines a shape; and
    the BTE storage device includes a storage area that defines a shape which corresponds to the shape of the BTE unit external housing.

11. A method as claimed in claim 10, wherein
    the BTE storage device storage area is slightly smaller than the BTE unit such that an interference fit is created when the BTE unit is placed into the BTE storage device.

12. A method as claimed in claim 1, wherein
    the exterior of the BTE unit external housing defines a shape; and the BTE storage device includes a storage area with an abutment having a shape that corresponds to the shape of the BTE unit external housing.

13. A method as claimed in claim 1, wherein the BTE storage device includes a storage area with a plurality of inwardly extending members that are configured to engage exterior of the BTE unit external housing.

14. A method as claimed in claim 13, wherein the inwardly extending members comprise resilient inwardly extending members.

15. A method as claimed in claim 1, wherein the BTE unit includes an auxiliary device connector.

16. A method, comprising the steps of:
removing an earhook from a behind-the-ear sound processor (BTE) unit that includes an external housing having an exterior with a shape, at least one user-manipulatable control element on the exterior of the external housing, a sound processor within the external housing that converts electrical signals from a microphone into a pulse sequence for a cochlear implant, a removable power supply mounted to the external housing, and the earhook;
placing the entire BTE unit but for the earhook into a BTE storage device that is not part of the BTE unit, BTE storage device including
   a storage portion with storage area that defines a shape which corresponds to the shape of the BTE unit external housing,
   a plurality of inwardly extending members within the storage portion that are configured to engage exterior of the BTE unit external housing,
   a cover portion,
   an opening into the storage area, and
   a resilient seal associated with the opening; and
connecting a headpiece that is configured to communicate with the cochlear implant to the BTE unit headpiece port by way of the resilient seal associated with the opening in such a manner that moisture is prevented from entering the storage portion by way of the opening.

17. A method as claimed in claim 16, wherein the headpiece is connected to the BTE unit by a cable; and the resilient seal associated with the opening engages the headpiece cable.

18. A method as claimed in claim 16, wherein the microphone is carried on the BTE unit.

19. A method as claimed in claim 16, wherein the microphone is carried on the headpiece.

20. A method as claimed in claim 1, wherein the cover portion has an open position and a closed position; and
the step of connecting a headpiece to the BTE unit comprises connecting a headpiece that is configured to communicate with the cochlear implant to the BTE unit when the cover portion is in the open position.

21. A method as claimed in claim 16, wherein the BTE unit includes an auxiliary device connector.

22. A method as claimed in claim 16, wherein the seal comprises a water-tight seal.

\* \* \* \* \*